(12) United States Patent
Dahm et al.

(10) Patent No.: US 7,211,433 B1
(45) Date of Patent: *May 1, 2007

(54) METHOD FOR THE ENRICHING OR DEPLETING TUMOR CELLS OBTAINED FROM A BODY FLUID AND KIT SUITABLE FOR THIS PURPOSE

(75) Inventors: Michael W. Dahm, Munich (DE); Robert C. Phelps, Karsfeld (DE); Carsten Brockmeyer, Holzkirchen (DE)

(73) Assignee: Hexal Gentech Forschungs GmbH, Holzkirchen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/890,649

(22) PCT Filed: Feb. 2, 2000

(86) PCT No.: PCT/EP00/00831

§ 371 (c)(1),
(2), (4) Date: Oct. 26, 2001

(87) PCT Pub. No.: WO00/46585

PCT Pub. Date: Aug. 10, 2000

(30) Foreign Application Priority Data

Feb. 3, 1999 (DE) ................................ 199 04 267

(51) Int. Cl.
*G01N 9/30* (2006.01)
*C12N 5/00* (2006.01)

(52) U.S. Cl. ...................... 435/325; 435/374; 435/377; 494/20; 422/72

(58) Field of Classification Search ................. 435/325, 435/374, 377
See application file for complete search history.

(56) References Cited

U.S. PATENT DOCUMENTS

| | | | |
|---|---|---|---|
| 3,741,400 A | 6/1973 | Dick | |
| 3,887,464 A | 6/1975 | Ayres | |
| 3,945,928 A | 3/1976 | Ayres | |
| 4,391,802 A * | 7/1983 | Suda et al. | 514/167 |
| 5,270,171 A | 12/1993 | Cercek et al. | |
| 5,474,687 A * | 12/1995 | Van Vlasselaer | 210/782 |
| 5,577,513 A | 11/1996 | Van Vlasselaer | |
| 5,629,147 A * | 5/1997 | Asgari et al. | 435/5 |
| 5,663,051 A | 9/1997 | Vlasselaer | |
| 5,807,744 A | 9/1998 | Berneman et al. | |
| 5,840,502 A | 11/1998 | Van Vlasselaer | |
| 5,932,427 A * | 8/1999 | Mond et al. | 435/7.24 |
| 5,962,237 A * | 10/1999 | Ts'o et al. | 435/7.23 |
| 6,051,393 A * | 4/2000 | Jones et al. | 435/29 |
| 2002/0098535 A1* | 7/2002 | Wang et al. | 435/40.5 |

FOREIGN PATENT DOCUMENTS

| | | |
|---|---|---|
| EP | 0 566 252 A2 | 10/1993 |
| EP | 0 875 202 A2 | 4/1998 |
| WO | WO 96/07097 | 3/1996 |
| WO | WO 97/21488 | 6/1997 |
| WO | WO 00/46585 A3 | 8/2000 |

OTHER PUBLICATIONS

U.S. Appl. No. 60/159,558.*
U.S. Appl. No. 60/119,460.*
The abstract of Soria (Clinical Cancer Research, May 1999, vol. 5, pp. 971-975).*
The Pharmacia Biotech Catalog, 1997, p. 5.*

* cited by examiner

*Primary Examiner*—Karen A. Canella
(74) *Attorney, Agent, or Firm*—Heller Ehrman LLP

(57) ABSTRACT

The invention relates to a method for the enrichment or depletion of tumor cells from a body fluid, in which a cell separation medium of specific density is overlaid with the body fluid and is centrifuged. A kit suitable for this method is likewise provided.

41 Claims, 12 Drawing Sheets

(continuation)

METHOD FOR THE ENRICHING OR DEPLETING TUMOR CELLS OBTAINED FROM A BODY FLUID AND KIT SUITABLE FOR THIS PURPOSE

The invention relates to a method for the enrichment or depletion of tumor cells from a body fluid and to a kit suitable therefor.

Virtually all solid malignant tumors have the potential to form metastases. The metastasis process comprises the spread of malignant cells as micrometastases, usually via the blood or lymph to remote organs and the development of autonomous secondary tumors. The extent of the filiarization determines the prognosis of an oncosis.

The requirements of tumor prevention or aftercare programs are to diagnose primary tumors or recurrences early, or metastases even before they become clinically manifest. This aim cannot yet be satisfactorily met with the available instrumental techniques. Detection of circulating tumor cells for example in peripheral blood would make it possible to initiate a possibly curative immunomodulating therapy or polychemotherapy at an early date, that is to say even before the appearance of a tumor which is noticed clinically. Quantification of tumor cells in peripheral blood before and after the therapy represents an important control in such cases.

Since body fluids generally contain a large number of widely differing cells, it is desirable before quantification of particular cell types, such as tumor cells, to enrich the latter and, at the same time, to deplete a maximum quantity of unwanted cells in order to facilitate the quantification.

In addition, a promising approach to the quantification of tumor cells is to determine the telomerase activity of a body fluid. For example, Kim et al. describe, in Science (1994) 266: 2011, an assay with which telomerase activities in tumor tissues can be determined.

However, in peripheral blood, an elevated telomerase activity is shown not only by tumor cells but also by hematopoietic stem cells and activated lymphocytes. Because of this fact it is necessary before detecting a telomerase activity as marker of disseminated circulating tumor cells in the blood to carry out a separation of the telomerase-active hematopoietic stem cells and lymphocytes from the tumor cells.

Besides the quantification of tumor cells in body fluids, however, histological examination thereof under a microscope may also be of interest, for example. In addition, tumor cells isolated under sterile conditions can be cultured in order to establish corresponding cell lines therefrom. Cell lines derived from disseminated circulating tumor cells instead of from solid tumors provide the opportunity of being able to investigate metastatic processes in a differentiated manner. In addition, the cell lines might contribute, for example, to the development of more effective tumor therapeutic agents.

For the enrichment of tumor cells it is possible, for example, for epithelial tumor cells to be labeled with the aid of specific antibodies against epithelial cell-specific antigens such as, for example, EPCAM (epithelial cell adhesion molecule), HEA (human epithelial antigen) and cytokeratin 7/8, and be coupled to magnetic particles or fluorescent molecules, and then be used for the enrichment by means of a cell separator such as MACS (magnetic cell sorting) or FACS (fluorescence activated cell sorting). However, the methods have the disadvantage that only tumor cells of epithelial origin are detected, but not, for example, melanoma cells. In addition, these methods are complicated and costly.

In the 1960s and 1970s, when methods like, for example, FACS or MACS were not yet available, tumor cells were separated from hematopoietic cells on the basis of their different density (J. A. Fleming et al., J. clin. Path. (1967), 20, 145). According to these data, tumor cells have a specific density of 1.040–1.080, whereas erythrocytes and polymorphonuclear leukocytes have a higher density. Lymphocytes by contrast have a specific density in the region of 1.060–1.075 and thus overlap with the specific density of tumor cells. Complete removal of lymphocytes, which likewise have telomerase activity, from tumor cells via differences in their densities therefore ought to be impossible. Thus, the use of a standard solution for isolating lymphocytes, such as, for example, Histoprep® (Sigma) with a density of 1.077 g/ml, also showed that lymphocytes from healthy blood donors with a density of up to 1.077 g/ml have telomerase activity.

Despite extensive research, it has not to date been possible to develop a simple, rapid and low-cost standard method for enriching tumor cells from body fluids, in which non-tumor cells with telomerase activity are also removed.

One object of the present invention is thus to provide a method for the enrichment or depletion of tumor cells from a body fluid which does not have the above-mentioned disadvantages and, in particular, is also able to remove non-tumor cells having telomerase activity from the required tumor cells.

It has now been found, surprisingly, that this object can be achieved by overlaying a cell separation medium with a density in the range from 1.055 to 1.065 g/ml with the body fluid containing tumor cells, and centrifuging. The use of the specific cell separation medium results in the cells present in the body fluid being fractionated in such a way that the lymphocytes enriched together with the tumor cells because of their density have no telomerase activity.

The present invention thus relates to a method for the enrichment or depletion of tumor cells from a body fluid, in which a cell separation medium is overlaid with the body fluid and centrifuged, wherein the cell separation medium has a density in the range from 1.055 to 1.065 g/ml.

It is self-evident that the method of the invention can be employed both for the enrichment and for the depletion of tumor cells, depending on which fraction is further processed after the centrifugation. No distinction will therefore be made hereinafter between these two possible further treatments; on the contrary mention will be made in general of enrichment with, however, both possibilities always being included according to the invention.

The enrichment method uses a cell separation medium as discontinuous gradient which is overlaid with the body fluid. Centrifugation fractionates the cells according to their specific cell density, and they can be removed in individual fractions. The specific degree of density of the cell separation medium allows tumor cells to be separated almost completely from the corpuscular portions present in the body fluids, specifically the cells of the red and white blood system. In addition, the method allows the separation of telomerase-positive from telomerase-negative hematopoietic cells, and the enriched tumor cells are present after the centrifugation in the same fraction as the telomerase-negative hematopoietic cells, so that subsequent detection of telomerase expression in this fraction can be attributed without doubt to the presence of tumor cells.

It is also surprising that a considerable reduction in the contaminating blood cells is achieved by a reduction which is only slight compared with the prior art in the density of the cell separation medium. This leads to a significant reduction in the total number of cells without significant losses of tumor cells occurring, which makes, for example, the screening of microscopic specimens considerably simpler and possible for the first time on the clinical scale.

It has been found that a particularly good separation efficiency, in the sense of an enrichment of tumor cells and a simultaneous depletion of unwanted blood cells, is achieved with a cell separation medium having a density in the region of 1.055–1.065 g/ml, preferably of 1.059–1.062 g/ml and particularly preferably of about 1.060 g/ml, in particular 1.060 g/ml±0.0005 g/ml.

It has also been found that the separation efficiency of the cell separation medium also depends on the age of the blood after blood sampling, and on the concentration of the anticoagulants added to the blood. It has also been found that with fresh blood, i.e. blood investigated on the same day (=24 hours) of blood sampling, a particularly good separation efficiency is achieved with a cell separation medium in the particularly preferred region of about 1.060 g/ml±0.0005 g/ml.

The centrifugation is advantageously carried out at about 500 to 2 000×g, preferably at about 1 000×g for about 10 to 30 minutes, preferably for 20–30 minutes. The temperature during the centrifugation is preferably about 4° C. This has the effect that the catalytic activity of proteases, DNAses and RNAses is kept as low as possible.

It is possible in principle to use as cell separation medium any suitable liquid of the required density. The cell separation medium ought not to react with the body fluid or the cells present therein. For example, Ficoll or Percoll or a Percoll- or Ficoll-like medium can advantageously be used, the solutions being in each case adjusted to the required density in accordance with the manufacturer's instructions. For example, the amount of Percoll stock solution with a density of 1.13 g/ml which is to be diluted to prepare 100 ml of a Percoll working solution of the required density (dd) is calculated by the formula:

$$100 \text{ ml} \times (dd - 0.106 - 0.9)/0.13$$

10% of the Percoll working solution of the required density always consists of a 10× physiological solution such as, for example, 10× PBS (phosphate-buffered saline solution), or of a 1.5M NaCl solution, in order to ensure a physiological osmolarity. The difference between the amount of Percoll stock solution (density 1.13 g/ml) calculated by the above formula with the saline solution and 100 ml is then made up with water.

It is thus possible to prepare a Percoll working solution with a density of 1.060 g/ml for example as follows:

| | |
|---|---|
| 41.54 ml | of the Percoll stock solution (density of 1.13 g/ml) |
| 48.46 ml | of $H_2O$ |
| 10.00 ml | of 1.5 M NaCl |
| 100.00 ml | of Percoll working solution, dd 1.060 g/ml |

The density of the cell separation medium is advantageously adjusted with the aid of a density meter (DMA 4500, Anton Paar, Austria) at the appropriate working temperature of 4° C.

In the subsequent cell separation, care should be taken that an ambient or working temperature of 8° C. is not exceeded. This would lead to a significant reduction in the Percoll density (compare FIG. 1) and to unwanted loss of cells.

The body fluid from which the tumor cells are to be enriched can be any human or animal body fluid or a dispersion of cellular tissue. Examples thereof are blood, in particular peripheral blood such as venous or arterial blood, lymph, urine, exudates, transudates, spinal fluid, seminal fluid, saliva, fluids from natural or unnatural body cavities, bone marrow and dispersed body tissue. The fluids from natural body cavities may be, for example, serous fluids such as peritoneal and pleural fluids, and the fluids from unnatural body cavities may be, for example, fluids from cysts.

Preferred body fluids are blood, bone marrow, lymph, serous fluids from body cavities, and urine, with particular preference for blood and urine. Urine is particularly suitable for enriching cells from bladder tumors.

However, the most preferred body fluid is peripheral blood, which is advantageously removed in an anticoagulant substance and is diluted with a diluent before overlaying the cell separation medium. It is possible to employ as anticoagulant substances, for example, EDTA or citrate or heparin or CPD (citrate, phosphate, dextrose) or comparable substances. Venous or arterial blood is suitable as peripheral blood.

The body fluid to be investigated is taken or collected in accordance with conventional standard protocols. Depending on the nature of the body fluid it is then either initially diluted with a diluent, preferably a buffer, or directly and undiluted overlaid on the cell separation medium in a centrifugation vessel. An alternative possibility is for the body fluid to be centrifuged beforehand at, for example, 1 000×g for about 10 minutes and, after resuspension of the cells in a buffer, to be overlaid on the cell separation medium. The buffer which is preferably used is Dulbecco PBS. A particularly suitable centrifugation vessel is a centrifugation vessel made of plastic such as, for example, polypropylene, in order to prevent nonspecific adsorption of cells. It should be possible to close the centrifugation vessel.

In a preferred embodiment of the method, the overlaying is preceded by addition to the body fluid of one or more substances which prevent aggregation of platelets onto tumor cells. These substances may, for example, be added together with the buffer used as diluent. Examples of suitable substances which prevent unwanted aggregation of platelets onto tumor cells are EDTA, citrate and ACD-A (acid citrate dextrose). In addition or instead thereof it is possible to remove substances which promote aggregation of platelets onto tumor cells from the body fluid before the overlaying. Examples thereof are ions such as magnesium and calcium ions.

The cell separation medium, which has a higher density than the body fluid to be investigated, is introduced into the centrifugation vessel and is then overlaid with the body fluid. Depending on the size of the centrifugation vessel and the volume of the body fluid from which the tumor cells are to be enriched, the cell separation medium can be introduced in a volume of 1–500 ml, for example.

It has proved to be particularly advantageous for the lower quarter of the centrifugation vessel to be briefly cooled intensively after the centrifugation and before removing the interphase enriched in tumor cells, in order to prevent contamination with cells. For example, the erythrocytes and leukocytes present in the cell pellet can be immobilized by cooling the lower quarter of the centrifugation vessel intensely in liquid nitrogen for 5–10 minutes. In the present case, the junction between the cell separation medium and the overlying body fluid is referred to as interphase. The tumor cells are enriched in this interphase and are collected after the centrifugation for example by aspirating off this phase. The intense cooling of the centrifugation vessel prevents mixing of the cells from the different phases, which allows false-positive test results to be precluded.

In order to ensure that the operations take place as simply as possible, in a preferred embodiment of the method of the invention it is possible to carry out the centrifugation in a vessel which is divided by a barrier, a filter or a sieve, called porous barrier or barrier hereinafter, into an upper and a lower compartment, the cell separation medium being introduced into the lower compartment, and the body fluid being put in the upper compartment. This prevents mixing of the body fluid to be investigated in the upper compartment with the cell separation medium in the lower compartment before and after the centrifugation step.

The position of the porous barrier in the centrifugation vessel can be chosen so that the liquid level of the cell separation medium comes to rest either exactly below, exactly within or exactly above the porous barrier.

The porous barrier can have, for example, a thickness of 0.5–10 mm, preferably of 1–5 mm. The porous barrier should additionally have a strength which allows it to withstand the centrifugal forces without damage.

Barriers preferably used have a porous nature which allows liquids and the corpuscular constituents of the blood, such as the cells of the red and white blood system, which have a higher density than the introduced cell separation medium, to be able to pass unhindered through the porous barrier during the centrifugation. The result of this is that the cell separation medium is forced during the centrifugation through the porous membrane into the upper compartment, and the tumor cells and platelets, which have a lower density than the introduced cell separation medium, come to rest at a level above the barrier. Porous barriers particularly suitable for this purpose have a pore size of 20–100 μm, preferably 20–30 μm.

The porous barrier can consist of any suitable material. Plastic, metal, ceramic or a mixture or special alloy of these materials are suitable, for example. However, it is also possible to employ any other natural or artificial material which is suitable.

In an embodiment of the method of the invention which is likewise preferred, the porous barrier consists of a hydrophobic material or is coated with a hydrophobic material.

As an alternative to the barrier in a centrifugation vessel it is also possible to employ a flap which, analogous to the barrier, divides the centrifugation vessel into an upper and lower compartment.

This flap has a nature which allows it to be tightly closed before and after the centrifugation and to be open only during the centrifugation due to the centrifugal force. During the centrifugation, with the flap open, the liquids in the lower and upper compartment come together. The result of this is that the cells of the red and white blood system, which have a higher density than the introduced cell separation medium, enter the lower compartment and displace the cell separation medium into the upper compartment. The effect of this is that the tumor cells, which have a lower density than the introduced cell separation medium, come to rest at a level above the flap.

It is possible and preferred to use as flap a material which has a higher density than the cell separation medium used and, at the same time, is so flexible that the flap can, during the centrifugation, open into the cell separation medium introduced into the lower compartment and, after the centrifugation, close again completely and tightly. Plastic or metal or a mixture or special alloy of these materials are suitable, for example. It is, however, also possible to employ any other natural or artificial material which is suitable.

The flap can have, for example, a thickness of 0.5–10 mm, preferably about 1–5 mm. The flap should additionally have a strength which allows it to withstand the centrifugal forces without damage.

In an embodiment of the method of the invention which is likewise preferred, the flap consists of a hydrophobic material or is coated with a hydrophobic material.

In a preferred use of the flap, attachment of the flap can take place in various ways: a) in analogy to the barrier rigidly connected to the centrifugation vessel, b) rigidly connected to the centrifugation vessel, where the centrifugation vessel itself can be dismantled into 2 parts, into an upper and into a lower part, and the flap forms the base of the upper part (FIG. 3), or c) rigidly connected to an insert which can be introduced into the centrifugation vessel, with the flap forming the base of the insert (FIG. 2).

The use of a flap in a divisible centrifugation vessel or in an insert allows a greater degree of automation and an improved sterile handling and has the advantage compared with the barrier that the cells present in the upper compartment after the centrifugation can be centrifuged directly into another vessel, 1) by placing the upper part of the centrifugation vessel on a new lower part or 2) placing the insert in a new centrifugation vessel.

It has proved to be advantageous for the method of the invention to use flaps which, during the centrifugation, open into the lower compartment not from their center but from their outer edges. The reason for this is that with flaps which open at the center the percentage of cells retained at the edges is undesirably high. The result of this is that these cells cannot be fractionated completely in accordance with their density and thus contaminate the enriched tumor cells in the upper compartment of the centrifugation vessel.

Thus, flaps preferred for the method of the invention are those which open into the lower compartment from their outer edges. It has emerged that this form of flap permit [sic] complete separation of cells according to their density. A corresponding wing flap is shown by way of example in FIG. 3.

It is possible with the aid of the porous barrier or flap to introduce the body fluid to be investigated into the centrifugation vessel without mixing it with the underlying cell separation medium and thus possibly impairing the enrichment or making it impossible.

After the centrifugation, the tumor cells present in the body fluid are located in the interphase of the upper compartment of the centrifugation vessel. About 80% of the liquid above the interphase can then be cautiously aspirated off and discarded. When blood is used as body fluid for example, this residual liquid is plasma, a plasma/PBS or plasma/buffer mixture containing the plasma proteins.

The remaining supernatant above the barrier or flap, in which the tumor cells are located, can subsequently be collected and, for example, transferred into a fresh centrifugation vessel (preferably made of optionally siliconized plastic and having the same volumetric capacity as the centrifugation vessel used previously).

The porous barrier or the closed flap prevents the cells in the upper and the lower compartment becoming mixed on removal of the remaining supernatant.

The upper compartment of the centrifugation vessel is then advantageously washed, for example twice, with a buffer, and the latter is likewise transferred into the fresh centrifugation vessel. Suitable buffers are, for example, Dulbecco's PBS (3.9 mM EDTA, pH 8.0 without calcium and magnesium) or NaCl/10% ACD-A (Guidelines for the collection, processing and storage of human bone marrow and peripheral stem cells for transplantation, prepared by the BCSH Blood Transfusion Task. Transfus. Med. 1994; 4: 165–72) or NaCl/5% ACD-A/1% albumin). It has proved to be particularly advantageous to add proteins such as, for example, 0.1% to 10% BSA (bovine serum albumin) to the buffer, because nonspecific binding of the cells to be collected to surfaces such as vessel wall, barrier or flap, pipette tips etc. is prevented. After a further centrifugation, for example at 1 000×g for about 10 minutes at a temperature of about 4° C., the collected cells can be, for example, supplied for tumor cell detection methods.

Since platelets are also enriched in the collected tumor cell fraction, it may be advantageous for the platelets to be washed twice more in a buffer (for example PBS with 0.1%–10% BSA) and be centrifuged at about 200×g and 10 minutes if the collected cells are, for example, to be placed on slides.

In order to improve the visibility of the cell ring containing the tumor cells after the centrifugation at the interphase between cell separation medium and body fluid for removal from the centrifugation vessel, it has proved to be advantageous to add a dye to the cell separation medium. It is possible to add, for example, 100 µl of a 1% Trypan blue solution to 100 ml of a Percoll working solution.

On use of a centrifugation vessel with porous barrier or flap, however, removal of the remaining supernatant liquid above the interphase is preferably followed by removal not just of the interphase but of all of the liquid remaining above the porous barrier, not because further cells are still present between interphase and porous barrier or flap, but because the removal makes it possible easily to mix the cells present in the cell ring. In order not to lose any cells from the upper compartment, the latter is advantageously washed twice more with a buffer (for example PBS with 0.1–10% BSA).

An alternative possibility on use of an insert or of a divisible centrifugation vessel is to centrifuge the cells located above the flap directly into a new centrifugation vessel. This takes place by introducing the insert into a new centrifugation vessel (FIG. 4) or fitting the upper part of the centrifugation vessel onto a new lower part.

It is possible with the method of the invention to enrich circulating tumor cells and, in particular, circulating tumor cells from solid tumors, i.e. non-hematological tumors, or hematological tumor cells, i.e. tumor cells of the red and white blood system.

It is possible with the tumor cell enrichment method of the invention for tumor cells to be separated, because of their different density, almost completely from the corpuscular constituents of body fluids such as, for example, the cells of the red and white blood system, and be concentrated and, for example, supplied for one of the known tumor cell detection methods.

The methods for detecting tumor cells encompass the entire range of current diagnostic methods. Examples thereof are microscopic, immunocytological/immuno-cytochemical, biochemical and/or molecular biological methods. For example, the tumor cells can be detected after the enrichment as whole cells or as cell constituents directly or after cell culture and expansion of the tumor cells by morphological, immunocytological/immunocytochemical, biochemical and/or molecular biological methods. These methods make it possible to detect a whole cell or the specific activity of a cell or to detect specific constituents of a whole cell. Examples of constituents of a whole cell are, inter alia, proteins and glycoproteins of the membrane, of the cytoplasm or of the cell nucleus, and the chromosomes, specific sections of chromosomes and even nucleic acid sequences such as DNA, RNA and cDNA.

Examples of direct cell detection methods are, inter alia, all types of microscopy including staining of cells or cell constituents. Examples of direct staining are Trypan blue staining or staining by specific antibodies which are directed against specific constituents of the cell such as the cell membrane, the cytoplasm or the cell nucleus, and onto which labeling signals such as, for example, fluorescent dyes are coupled. Detection methods are, inter alia, flow cytometry or FACS (fluorescence activated cell sorting), ELISA and Western blotting. Further methods for detecting cell constituents are, inter alia, methods for detecting nucleic acids with the aid of labeled probes, for example FISH, in situ hybridization, Northern, Southwestern and Southern blotting or differential display, and, inter alia, the methods for amplifying nucleic acids, inter alia PCR, RT-PCR, in situ RT-PCR and NASBA.

It is advantageous furthermore to employ methods which make a specific binding of an antibody to a protein or of an oligonucleotide to a nucleic acid (DNA, RNA or cDNA) visible through amplification of the signal. One example thereof is the use of specific dendrimers (Polyprobe) (cf. U.S. Pat. No. 5,487,973 and Nilsen, T. W., Grayzel, J. and Prensky, W. (1997) J. theor. Biol. 187: 273–284). Dendrimers are highly branched structures which preferably consist of nucleic acids and are derived from the sequential hybridization of monomeric structures. A monomer is a heterodimer which consists of two single-stranded nucleic acids which form a double-stranded waist and four single-stranded arms. A dendrimer is made up by sequential binding of such monomers in a plurality of binding planes: the first binding plane consists of four monomers with twelve single-stranded arms. The second plane consists of twelve monomers with 36 single-stranded arms. The sixth plane consists of 972 monomers with 2916 free single-stranded arms. On one of these single-stranded arms it is possible to couple on the one hand specific antibodies or specific probes such as nucleic acids. On the other single-stranded arm it is possible on the other hand to couple specific labeling signals such as, for example, fluorescent dyes, or radioactive substances. The use of the dendrimers for detecting rare DNA or RNA can take place either directly or indirectly after amplification by, for example, PCR, RT-PCR or NASBA.

The subsequent detection methods can be employed in the following areas:

The detection of the tumor cells can be employed directly as tumor marker.

In staging investigations, the number of detected circulating tumor cells can be correlated with the clinical picture, and an individual tumor staging can be established. After removal of the primary tumor, the patient can be subjected to regular checks for recurrence and be immediately treated if there is a positive finding. Further possible applications are the detection of residual tumor cells in the bone marrow of patients who have to undergo high-dose radiotherapy or of circulating tumor cells within the framework of ex vivo and in vivo gene therapy approaches.

The obtaining of circulating tumor cells makes it possible for therapies to be examined for their efficacy and, where appropriate, modified. This is possible in particular since, after obtaining tumor cells, directly or after culturing and expansion, the individual resistance status of the tumor cells in relation to a cytostatic can be checked and alternative products can be tested. An additional possibility is to test novel therapeutic agents on the tumor cells obtained.

The method is ascribed a particular value within the framework of tumor prevention investigations since longer survival rates are to be expected with considerably earlier diagnosis and immediate therapy. Further applications are in the production of tumor vaccines and gene therapy.

The present invention thus also relates to a method for detecting tumor cells in a body fluid, in which the tumor cells are enriched from the body fluid as described above and, preferably at the same time, unwanted cells are depleted.

In immunocytological/immunocytochemical diagnosis, for example, circulating tumor cells are detected in blood and bone marrow by specific antibodies. For this purpose, about $1-2 \times 10^6$ mononuclear cells (MNC) are put by means of a centrifuge on a slide, stained and evaluated microscopically (Zhong et al. Tumordiagn. u. Ther. (1999) 20: 39). A blood sample contains between [sic] $1-3 \times 10^6$ MNC/ml. Based on an average amount of $2 \times 10^6$ MNC/ml, 20 ml of blood contain about $40 \times 10^6$ MNC, which would have to be investigated on 20–40 slides. Our investigations show that about $1 \times 10^5$ cells can be enriched from 20 ml of blood using the method of the invention. This means that evaluation of the tumor cell fraction obtained from up to 200 ml of blood or bone marrow can take place on one specimen.

This example makes it clear that the method of the invention has crucial importance especially in relation to the following factors: 1. economy: saving of time and reagents, 2. quality of the results: for example through the increase in the signal/noise ratio, 3. opening of previously impossible cytobiological or molecular biological investigations on circulating tumor cells: for example single-cell PCR, FISH and gene array scanner analyses and 4. automation and miniaturization of the detection methods: for example HTS (high throughput [sic] systems) and nanotechnology.

Since the probability of obtaining a positive finding within the framework of manifest micrometastasis is significantly improved, the method of the invention additionally has crucial advantages in relation to a standardization of the detection of tumor cells both in bone marrow and in peripheral blood, as required, for example, by the ISHAGE (International Society for Hematotherapy and Graft Engineering [sic]) Working Group for Standardization of Tumor Cell Detection in Borgen et al. in Cytotherapy (1999) 1: 377.

As mentioned, it is possible to automate single steps or a plurality of single steps within the enrichment method of the invention or the entire method itself. All technical methods in which the necessary manipulation can be carried out automatically by robots or specifically designed machines under standardized conditions are suitable for automating the method. Also suitable are systems in which the individual reaction steps can be carried out in minimal volumes. Examples thereof are high throughput systems (HTS) and nanotechnology systems.

For example, the use of microtiter plates permits a greater degree of automation. For the purposes of the enrichment method of the invention it is possible, for example, for the entire range of current diagnostic methods such as, for example, microscopic, immuno-cytological/immunocytochemical, biochemical and/or molecular biological methods to be carried out at the microtiter plate level. Microtiter plates permit the same manipulations for the skilled worker, with the difference that a plurality of samples can be processed simultaneously under standardized conditions and in faster periods.

For the purpose of automating the method of the invention, for example, for the immuno-cytological/immunocytochemical detection it is possible for different blood or bone marrow samples, after fractionation has taken place, to be processed separately to a cytospin preparation or, alternatively, be centrifuged directly on microtiter plates. A cytospin preparation has a basic area of about 240 mm$^2$ onto which $1 \times 10^6$ cells are centrifuged. Suitable microtiter plates are, for example, 12-chamber, 24-chamber or 48-chamber plates with a chamber area of in each case respectively about 350 mm$^2$, 190 mm$^2$ and 110 mm$^2$.

12-chamber or 24-chamber plates are preferably used, and 24-chamber plates are particularly preferably used, for the immunocytological/immunocytochemical diagnosis. It is further preferred to use microtiter plates in which the chambers can be employed as strips in a frame, for example 3 strips of 4 chambers/12-chamber, 4 strips of 6 chambers/24-chamber and 6 strips of 8 chambers/48-chamber plate.

Particularly preferred microtiter plates are those which have a glass base instead of a plastic base, because glass is more suitable than plastic for various applications (for example for immobilizing the cells). In analogy to the cytospin preparations, computer-assisted image analysis is possible for evaluation of the preparations in microtiter plates.

In analogy to the methods in the area of immunocytology/immunocytochemistry, it is likewise possible to carry out the molecular biological diagnostic methods on microtiter plates, with the difference that, after fractionation of the cells, considerably smaller volumes are processed and thus it is possible to use microtiter plates up to HTS (high throughput system) microtiter plates or nanotechnology systems, and the manipulations can be carried out by robots or specifically designed machines under standardized conditions in minimal volumes.

Within the framework of automation of the method according to the invention, inserts can be placed on the microtiter plates which permit the possibility of carrying out the fractionation of the cells in smaller volumes, in analogy to a centrifugation vessel, directly on a microtiter plate. An attachment of this type, in which the individual chambers are provided with flaps in analogy to the centrifugation vessels described, is depicted by way of example in FIG. 5 for improved understanding.

The present invention thus also relates to methods for the semiautomatic or completely automatic detection of tumor cells in a body fluid, in which the tumor cells have been enriched from a body fluid as described above.

In a special application of the method of the invention it is also possible for tumor cells to be isolated from body fluid and cultivated for example for research and therapy purposes. All systems as well as nanotechnology systems are suitable for the culturing. The culturing of tumor cells can be carried out semiautomatically or completely automatically in these systems under optimized conditions in minimal volumes.

The present invention thus also relates to methods for culturing tumor cells which have been obtained by use of the method of the invention.

In a specific application of the method of the invention it is also possible for tumor cells to be depleted for example from the bone marrow or from the peripheral blood, for example if the donor has been treated with growth factors for the purpose of increasing the blood stem cell content.

An enrichment of blood stem cells both from the blood and from the bone marrow is routinely carried out for the purpose of blood stem cell transplantation. These blood stem cells may be the patient's own (autologous) or foreign ones (allogeneic). Autologous and allogeneic blood stem cell transplantation is applied in particular within the framework of high-dose therapy (for example chemotherapy or radiotherapy) of oncoses and for the therapy of disorders of the hematopoietic system and of autoimmune diseases (for example rheumatism). In the case of enrichment of blood stem cells from the bone marrow, the starting material is obtained directly by removing bone marrow, for example from the iliac crest. In the case of enrichment of blood stem cells from the peripheral blood, the concentration of blood stem cells in the blood is first increased by administration of growth factors. Mononuclear cells (MNC) are subsequently obtained by leukapheresis. The mononuclear cells obtained are then subjected to an enrichment method for blood stem cells. This enriched blood cell fraction is then mixed with DMSO and frozen until transplanted.

In the case of autologous blood stem cell transplantation, the risk of transplanting contaminating tumor cells is particularly high and endangers the success of the therapy. It is therefore desirable before the transplantation to examine the MNC fraction obtained for the presence of tumor cells and to deplete tumor cells which are present.

It has now been found that blood stem cells which carry as surface marker the CD34 antigen are telomerase-positive and have a density of about 1.061 g/ml±0.0005 g/ml. This density is so close to the particularly preferred density of 1.060 g/ml±0.0005 g/ml used in the method of the invention for the enrichment of tumor cells that perfect separation of telomerase-positive tumor cells from telomerase-positive non-tumor cells after a therapeutic mobilization of CD 34+ blood stem cells into the peripheral blood cannot always be ensured completely and reliably.

In the case of telomerase detection from the peripheral blood, experiments which have been carried out prove that the cell fraction collected from the interphase, even after a fractionation with a cell separation medium with a density of 1.065 g/ml, was telomerase-negative for all blood samples from the subjects investigated. This means that in the subjects investigated the proportion of CD 34+ cells, or the telomerase activity of the CD 34+ cells, in the peripheral blood was below the detection limit (example 2).

After mobilization of blood stem cells into the peripheral blood it is probable that the collected cell fraction on separation with a density of 1.060±0.0005 g/ml will be telomerase-positive and it is no longer possible to distinguish between telomerase-positive tumor cells and telomerase-positive non-tumor cells. The reason for this is that owing to the stimulation with the growth factors on the one hand the amount of the CD 34+ blood stem cells has increased, and on the other hand the telomerase activity of these cells has increased. There is incomplete depletion of some of these CD 34+ blood stem cells, and thus the telomerase-positive tumor cells present in the interphase are contaminated by telomerase-positive CD 34+ non-tumor cells.

This problem can be solved according to the invention by modifying in this case the method described above in such a way that, in a first step, the CD 34+ blood stem cells are enriched and the unwanted blood cells are depleted to a large extent. Then, in a second step, either the tumor cells are separated from the CD 34+ blood stem cells or the CD 34+ blood stem cells are separated from the tumor cells by immunoadsorption. It has been found that a particularly good separation efficiency, in the sense of depletion of unwanted blood cells with, at the same time, enrichment of CD34+ positive blood stem cells and tumor cells, is achieved by increasing the density of the cell separation medium to a range from 1.061 to 1.065 g/ml and particularly preferably of about 1.062 g/ml, in particular 1.062 g/ml±0.0005 g/ml.

The second separation step takes place by further enrichment of the required cell populations or depletion of unwanted cells such as, for example, tumor cells in blood stem cell preparations for diagnostic like therapeutic purposes, and is carried out by a subsequent enrichment or depletion method, for example using immunoadsorption methods with specific antibodies.

By means of the separation method of the invention it is possible to apply a subsequent depletion method at considerably lower cost after there has already been depletion of a considerable proportion of the unwanted blood cells.

The present invention thus also relates to a method in particular for the detection and for the therapeutic depletion of tumor cells from blood stem cells of bone marrow and peripheral blood, in which the tumor cells and blood stem cells are enriched in a fraction as described above, and the blood stem cells or tumor cells are either enriched or depleted in a second step.

Since the method of the invention can advantageously be employed within the framework of obtaining therapeutic autologous blood stem cells, it is obvious also to employ this method for obtaining allogeneic blood stem cells.

The method of the invention for enrichment of allogeneic and autologous blood stem cells has the effect that the blood stem cells are enriched considerably better and unwanted blood cells are depleted considerably better than can be carried out with the methods customary to date. This has the particular advantage that the amount of DMSO necessary for cryopreservation of the cells can be reduced considerably. It is thus possible to reduce the complications which are caused by DMSO and arise on transplantation of the blood stem cells.

The present invention thus also relates to a method for the therapeutic enrichment of allogeneic or autologous blood stem cells from bone marrow and peripheral blood, in which in the obtaining of the autologous blood stem cells the tumor cells and blood stem cells are enriched in a fraction as described above, and the blood stem cells or tumor cells are either enriched or depleted in a second step.

A further aspect of the present invention is a kit for the enrichment of tumor cells from a body fluid which is suitable for carrying out the method of the invention. For this purpose, the kit comprises a cell separation medium which has a density in the range from 1.055 to 1.065 g/ml, preferably in the range from 1.057 to 1.063 g/ml, more preferably from 1.059 to 1.061 g/ml and particularly preferably of about 1.060 g/ml, in particular 1.060 g/ml±0.0005 g/ml, and, where appropriate, a centrifugation vessel.

A further aspect of the present invention is a kit for the enrichment of blood stem cells from peripheral blood and the bone marrow, which is suitable for carrying out the method of the invention. For this purpose, the kit comprises a cell separation medium which has a density in the range from 1.061 to 1.065 g/ml and preferably of about 1.062 g/ml, in particular 1.062 g/ml±0.0005 g/ml, and, where appropriate, a centrifugation vessel.

In order to facilitate routine work with the kit, the centrifugation vessel can have a porous barrier or flap, preferably with a thickness of 1–10 mm, preferably about 1–5 mm, which divides the centrifugation vessel into an upper and a lower compartment. The porous barrier can advantageously have a pore size of 20–100 μm, preferably 20–30 μm, and preferably consists of a hydrophobic material.

The flap advantageously opens from its outer edges into the lower compartment and preferably consists of a hydrophobic material. The flap is moreover, in analogy to the barrier, a) rigidly connected to the centrifugation vessel, b) rigidly connected to the centrifugation vessel where the centrifugation vessel itself can be dismantled into 2 parts, into a lower and into an upper part, and the flap forms the base of the upper part, or c) rigidly connected to an insert which can be introduced into the centrifugation vessel, with the flap forming the base of the insert.

The size of the centrifugation vessel present in the kit should be appropriate for the amount of body fluid from which the tumor cells are to be enriched. For example, the centrifugation vessel can have a volume of 1–500 ml, preferably 1–50 ml and particularly preferably 15–50 ml. The centrifugation vessel can preferably be closed. The centrifugation vessel is preferably sterile or sterilizable and can moreover consist of solid undeformable or else deformable materials (bag) or be a microtiter plate.

In an alternative embodiment, the size of the centrifugation vessel present in the kit should suit the amount of body fluid from which the blood stem cells are to be enriched. For example, the centrifugation vessel can have a volume of 50–500 ml, preferably 50–250 ml and particularly preferably 50–200 ml. The centrifugation vessel can preferably be closed. The centrifugation vessel is sterile or sterilizable and can moreover consist of solid undeformable or else deformable materials (bag).

The cell separation medium in the kit is particularly advantageously already present in the lower compartment of the centrifugation vessel so that the latter can be employed simply and rapidly in routine investigations.

In another preferred embodiment, the kit comprises a cell separation medium which is mixed with a dye which makes the interphase between cell separation medium and the interphase more easily visible after the centrifugation.

Finally, the invention also advantageously includes centrifugation vessels which can be employed for the enrichment or depletion method of the invention and which have a flap as described above.

The method of the invention has the advantage that telomerase-positive non-tumor cells can easily and reliably be separated from the tumor cells to be enriched, so that no false-positive results are obtained in the subsequent detection method due to telomerase-active non-tumor cells. In addition, only a few working steps are necessary for the enrichment and isolation of tumor cells from body tissue, so that this makes it possible to process larger amounts of sample material. The costs for the necessary materials are significantly lower for example compared with the use of specific antibodies and the subsequent separation using suitable apparatuses.

In addition, the investigation of 10 different cell lines derived from tumor tissues, such as melanoma, prostate, breast, lung, liver and colorectal carcinomas, showed that the majority of the cells from all these cell lines were enriched by the method of the invention.

The appended figures show:

FIG. 1 the result of an investigation of the temperature-dependence of the density of Percoll. The density of the prepared Percoll working solution in a temperature range of about 0° C.–8° C. is 1.060±0.005 g/ml. At an ambient temperature of more than 8° C., the Percoll working solution starts to expand continuously, and the density originally set to decrease significantly.

FIG. 2 shows an example of a centrifugation vessel (1) with a closure (2) and an insert (3) with a flap (4) which is fixed to a transverse strut (5). The transverse strut (5) is firmly connected to the insert (3). The flap (4) forms the base of the insert (3). In the simplest case, the flap is, for example, a disk which is bent by the centrifugation on two sides across the transverse strut (5) into the introduced cell separation medium. The transverse strut (5) also assists complete closure of the flap after the centrifugation. The centrifugation vessel (1) must be closed by the closure (2) during the centrifugation in order to prevent the introduced cell separation medium being forced upward at the gap (s) between centrifugation vessel (1) and insert (3). In addition, the flap (4) can be provided, for example with two additional feet (6) so that the insert (3) can be put down upright on the transverse strut (5) and the feet (6). At the same time, the feet (6) assist opening of the flap because they provide additional weight on the outer edges of the flap (4).

FIG. 3 shows an example of a centrifugation vessel (7) which differs from the centrifugation vessel (1) shown in FIG. 2 consisting of two parts. The upper part (8) can be fitted onto a lower part (9). The flap (4) forms the base, and the closure (2) the lid, of the upper part.

FIG. 4 shows an example of the mode of functioning of a flap insert in a centrifugation vessel as used, for example, for separating tumor cells from blood or bone marrow. a) The sample of blood or bone marrow (bk) to be investigated contains, described simply, erythrocytes (rbc), leukocytes (wbc) and tumor cells (tc) and after removal is placed directly in the insert (3) whose base is tightly closed by the flap (4). b) The insert (3) is then introduced, for example, into a 50 ml centrifugation vessel (1) into which an appropriate volume of the cell separation medium (sm) has already been introduced. c) During the centrifugation, owing to the centrifugal force applied, the two sides of the flap (4) are bent across the transverse strut (5) downward into the cell separation medium (sm). This has the effect that the liquids (bk) and (sm) meet, and the cell separation medium (sm) is forced upward through the denser cells (rbc) and (wbc), leading to the tumor cells (tc), which have a low [sic] density than the introduced cell separation medium (sm), coming to rest at a level above the flap (4). d) After the centrifugation, the flap (4) is tightly closed again so that e) the insert (3) with the tumor cells (tc) a small proportion of cell separation medium (sm) and plasma (p) can be transferred f) and g) into a new centrifugation vessel. Renewed centrifugation h) results in the tumor cells (tc) being pelleted i) and they can then j) be further purified and supplied for subsequent investigations.

The following examples are intended to explain the invention in more detail.

EXAMPLE 1

Venous blood (5–20 ml) in a siliconized plastic centrifugation vessel was mixed with EDTA (3.9 mM final concentration, pH 8.0) and then with 1 volume of PBS. The blood/PBS mixture was subsequently put onto 5–10 ml of Percoll with a density of 1.065 g/ml and centrifuged with slow acceleration and without brake for 30 minutes at 1 000×g and 4° C. The lower quarter of the centrifugation vessel was then incubated in liquid nitrogen for 5–10 min. This prevented contamination with cells of the pellet while the cells located at the interphase at the junction between the Percoll and the overlying plasma/PBS mixture were being aspirated off. The interphase cells, which were mainly platelets and tumor cells circulating in the blood, were then transferred into a new siliconized plastic centrifugation vessel and centrifuged at 1 000×g and 4° C. for 10 min. For the subsequent RT-PCR investigation, the cell pellet was taken up in a guanidium isothiocyanate buffer, whereby the cells were lysed and could be subjected to RNA isolation.

EXAMPLE 2

It was shown with the aid of so-called spiking experiments, in which tumor cells of various cell lines were mixed with blood from normal donors, and the tumor cells were then reisolated and investigated in the RT-PCR, that, depending on the cell line used, the telomerase activity of about 1–4 spiked tumor cells/ml of blood can be detected. The RT-PCR was carried out in analogy to the procedure described in example 4.

For this purpose, the cells of the tumor cell lines to be spiked were cultivated to confluence in accordance with the manufacture's instructions (ATCC, *American Tissue Cell Culture*). The cells were subsequently trypsinized and washed in medium (RPMI 1640). After removal of a 10 μl aliquot, which was mixed 1:1 with Tryptan blue, the live cells were determined in a counting chamber and the corresponding cell concentration was calculated. The cell suspension was then diluted, and a volume corresponding to a particular number of cells was mixed with the blood from healthy blood donors. Blood to which no tumor cells were added served as control. The enrichment of the spiked tumor cells was carried out once for comparison with a cell separation medium having a density of 1.070 g/ml and by the method of the invention. The recovery rate was determined by subsequently carrying out microscopic, flow cytometry and RT-PCR analyses.

a) Comparative Experiment

Figure 6:
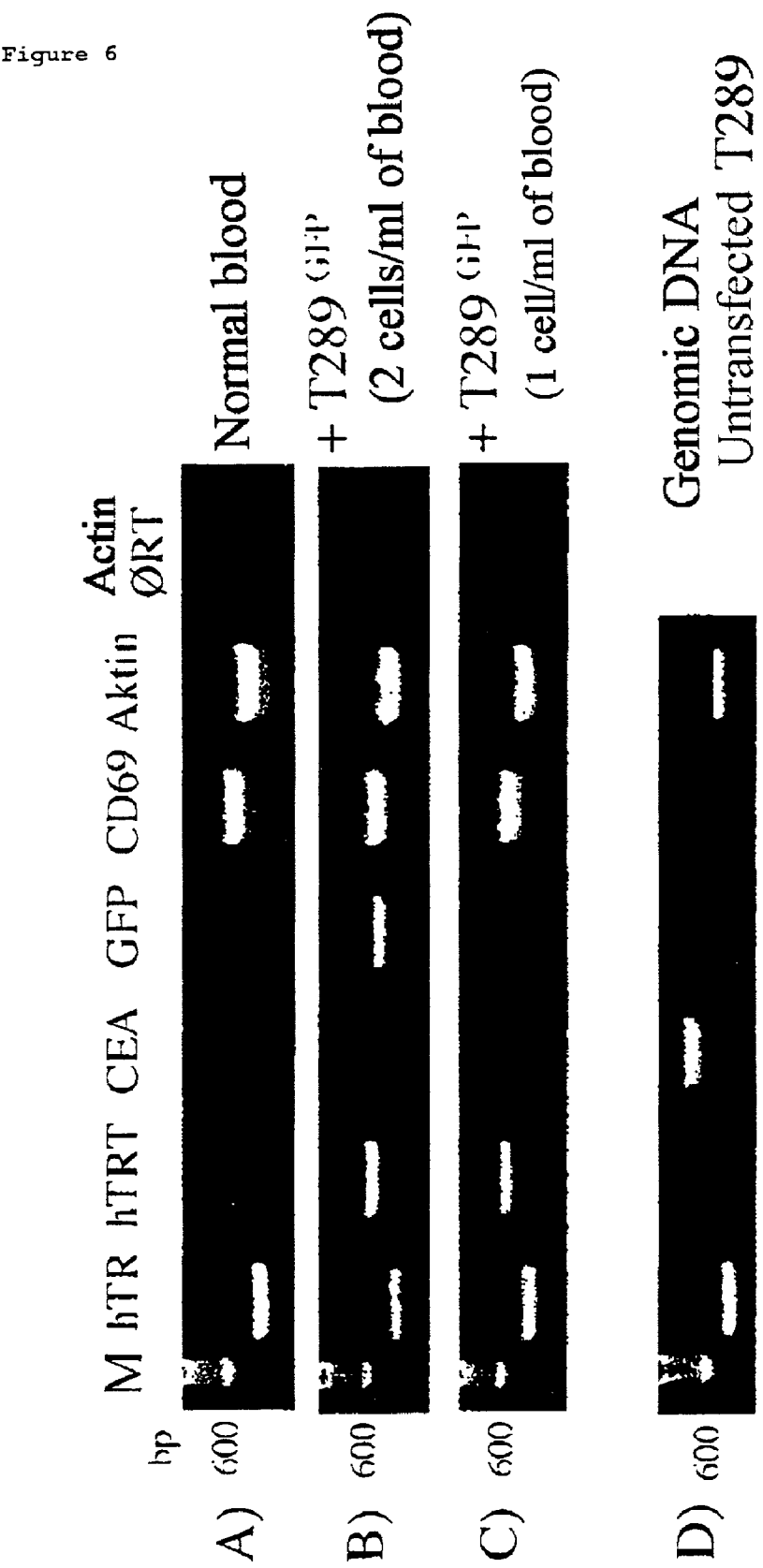
FIG. 6 shows the result of an RT-PCR analysis of blood from a healthy donor (A) and blood from the same donor mixed with GFP-transfected cells of the melanoma cell line T289 (B, C) after enrichment of tumor cells with a cell separation medium having a density of 1.070 g/ml.

FIG. 6 shows the result of an RT-PCR analysis of 20 ml of blood from a healthy donor (A) and 20 ml of blood from the same donor mixed with GFP-transfected cells of the melanoma cell line T289 (B, C). The blood was layered on Percoll having a density of 1.070 g/ml and centrifuged, and the cells were then analyzed. The catalytic subunit of telomerase (hTRT) is undetectable in normal blood (A), whereas hTRT is detectable with 1 and 2 spiked melanoma cells per ml of blood (B, C). With the Percoll density of 1.070 g/ml used, however, there is still a sufficient number of telomerase-active leukocytes present in the interphase, which makes the RNA component (hTR) also detectable in unspiked blood. The presence of activated and probably therefore also telomerase-active leukocytes in the fraction of isolated cells is also indicated by the fact that CD69, an early activation marker in B and T cells, is detectable in all blood samples (A–C). The tumor marker CEA (carcinoembrionic antigene) is negative both in unspiked and in spiked blood (A–C). GFP (green fluorescent protein), which was used as additional marker for the spiked tumor cells, is not detectable in unspiked blood (A). Since only about 50% of the transfected T289 melanoma cells express GFP, the protein is detectable only in up to 2 spiked tumor cells per ml of blood (B). Actin served as RT-PCR positive control (actin) and in the mixture without RT reaction as negative control (actin ØRT). PCR amplification of genomic DNA from untransfected T289 cells leads to no amplicons with the specific primer pairs for hTRT, GFP and CD69.

B) Experiment According to the Invention

Figure 7:
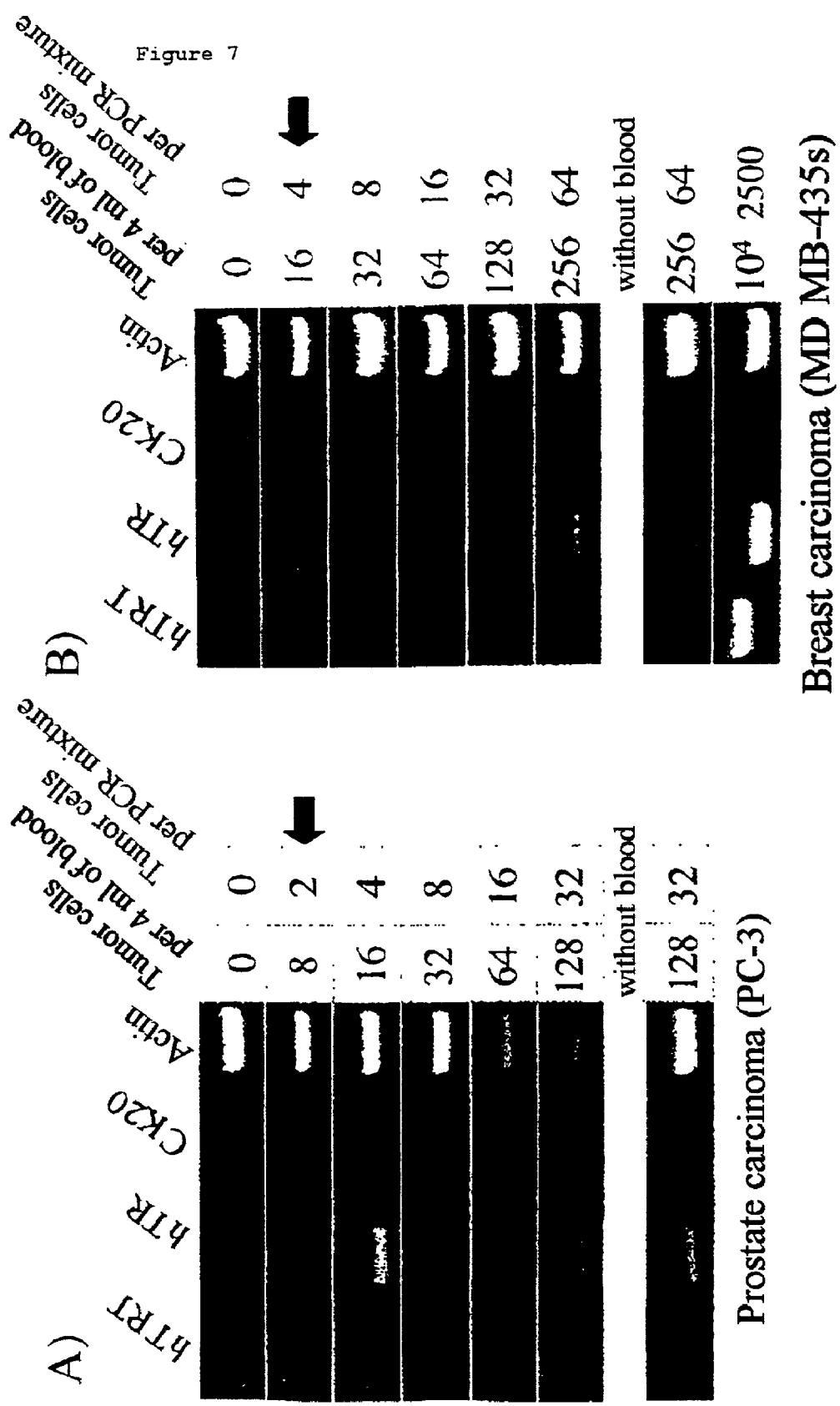
FIG. 7 shows the result of an RT-PCR analysis of blood from healthy donors which was mixed with tumor cells of a prostate carcinoma (A) and breast carcinoma cell line (B), after enrichment of tumor cells with a cell separation medium having a density of 1.065 g/ml.

FIG. 7 shows RT-PCR analyses of blood from healthy donors which was mixed with tumor cells from the prostate carcinoma (A) and breast carcinoma cell line (B), layered onto Percoll having a density of 1.065 g/ml, centrifuged and then analyzed.

Figure 1:
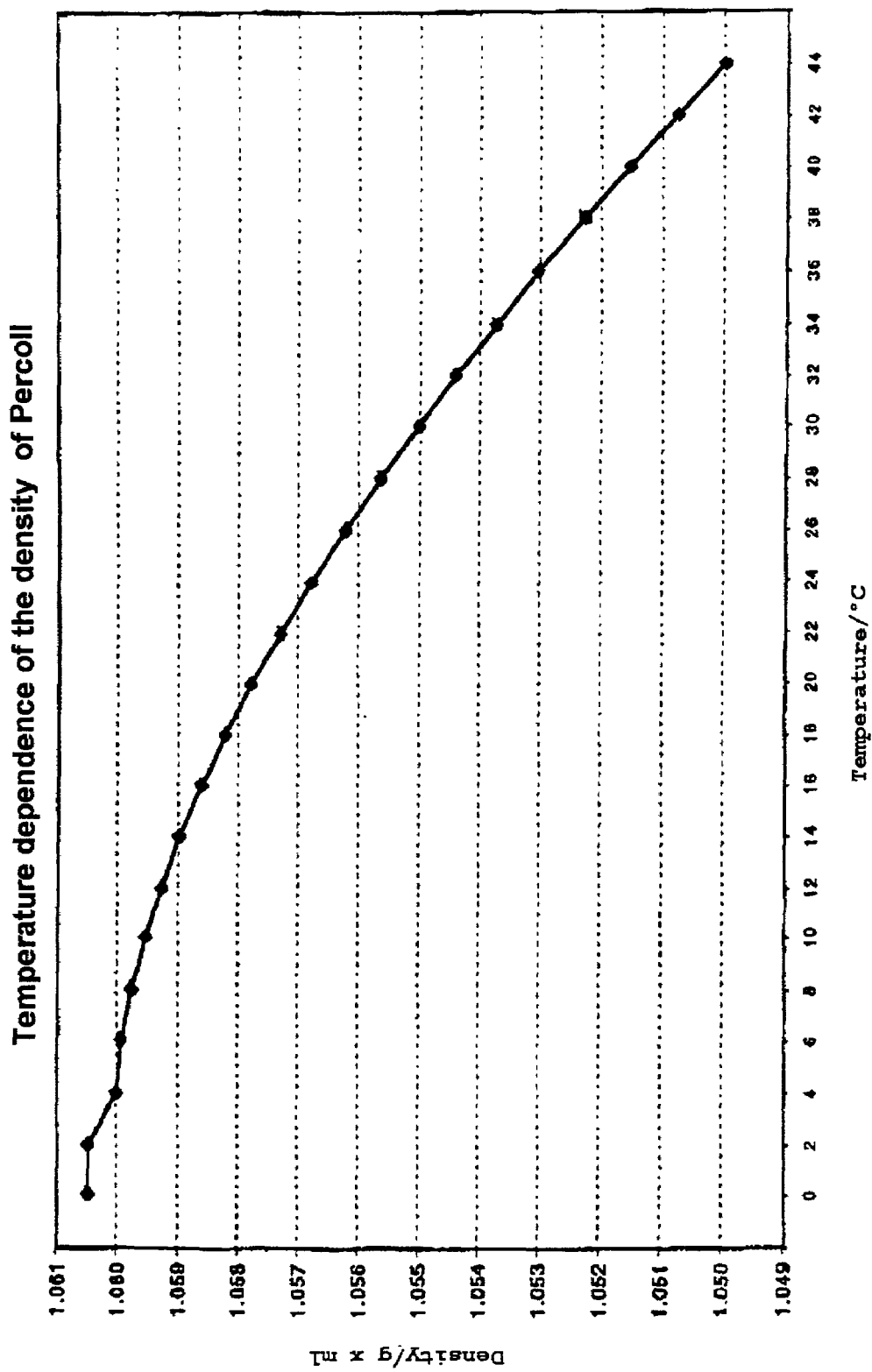
Figure 2:
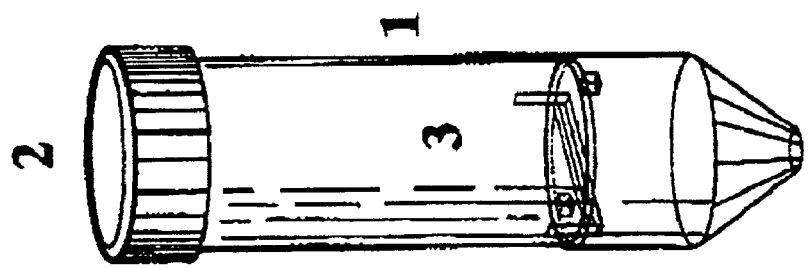
Figure 2:
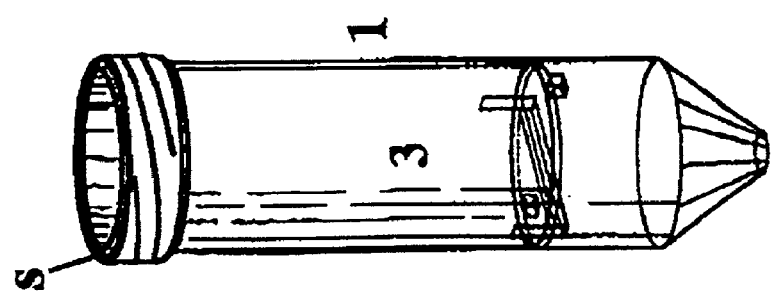
Figure 2:
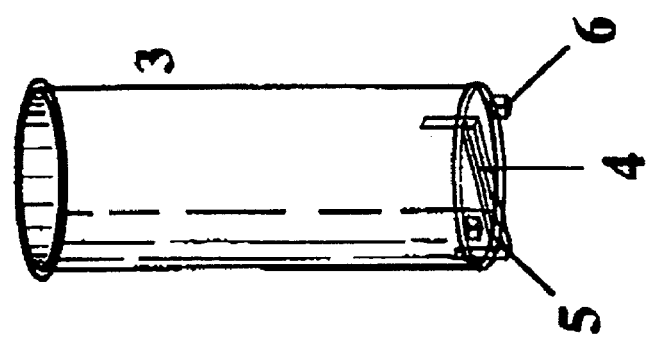
Figure 2:
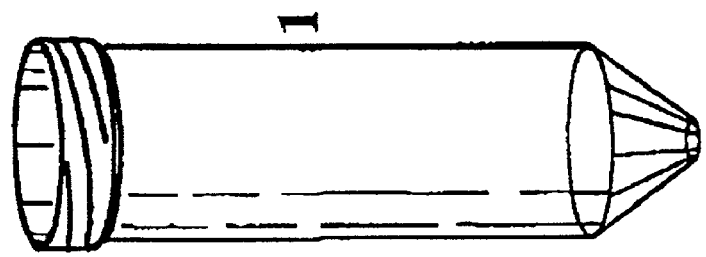
Figure 3:
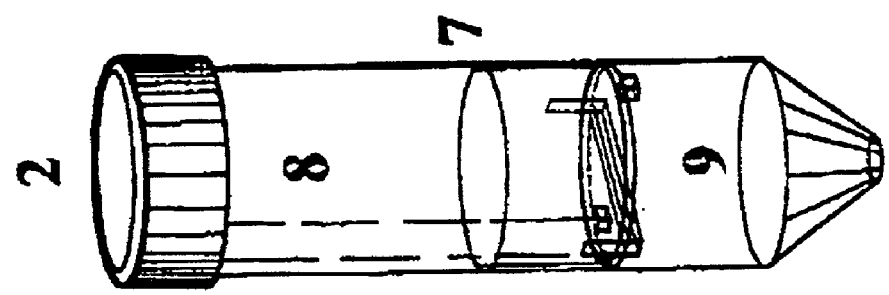
Figure 3:
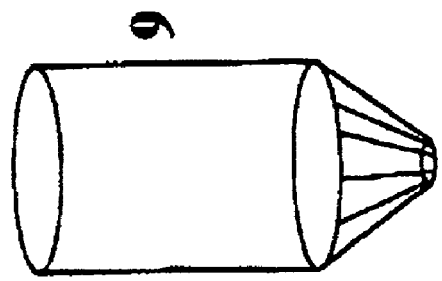
Figure 3:
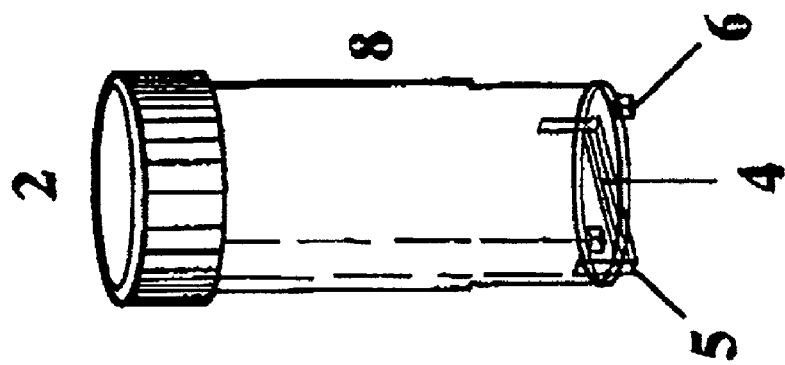
Figure 4:
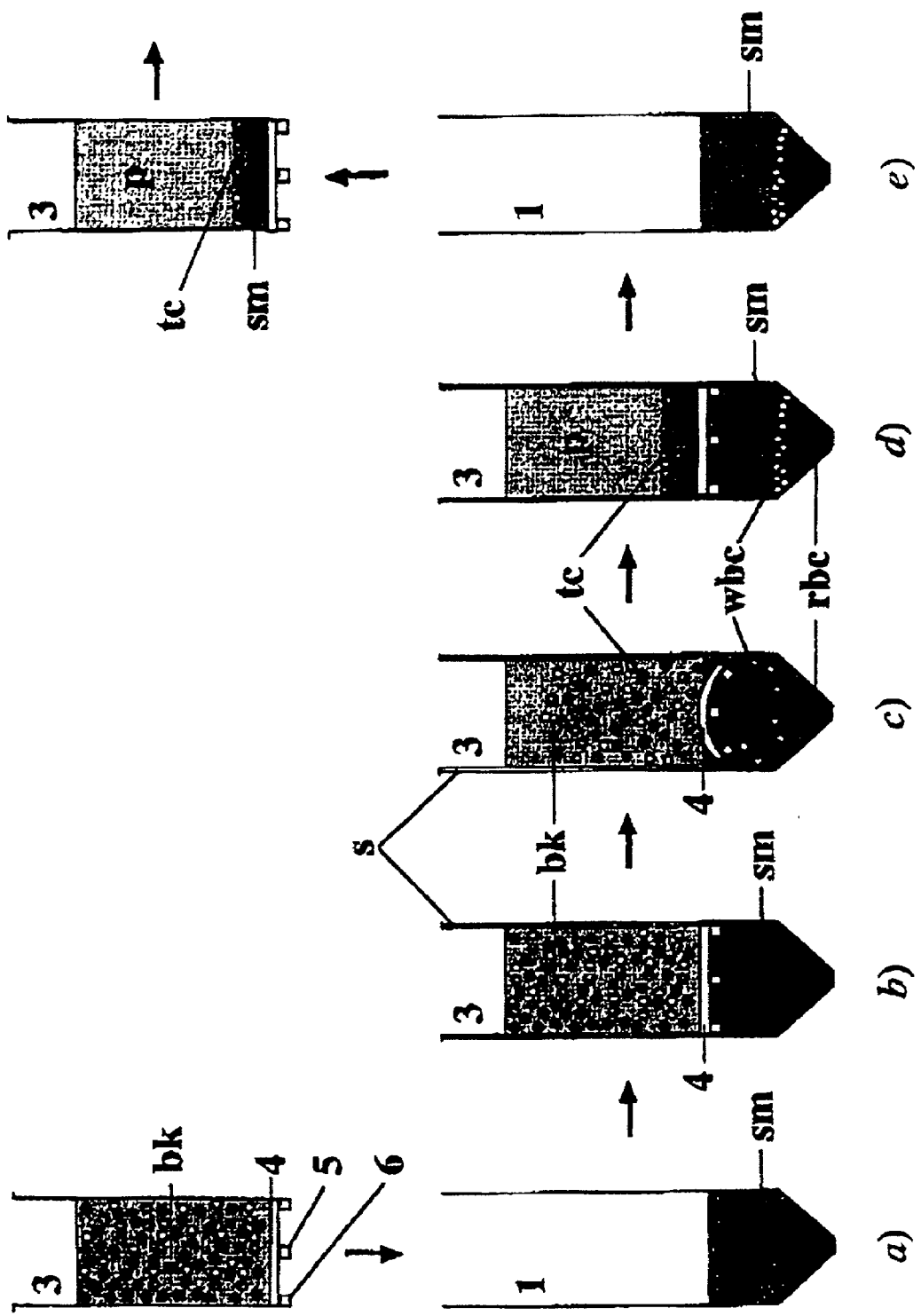
Figure 4:
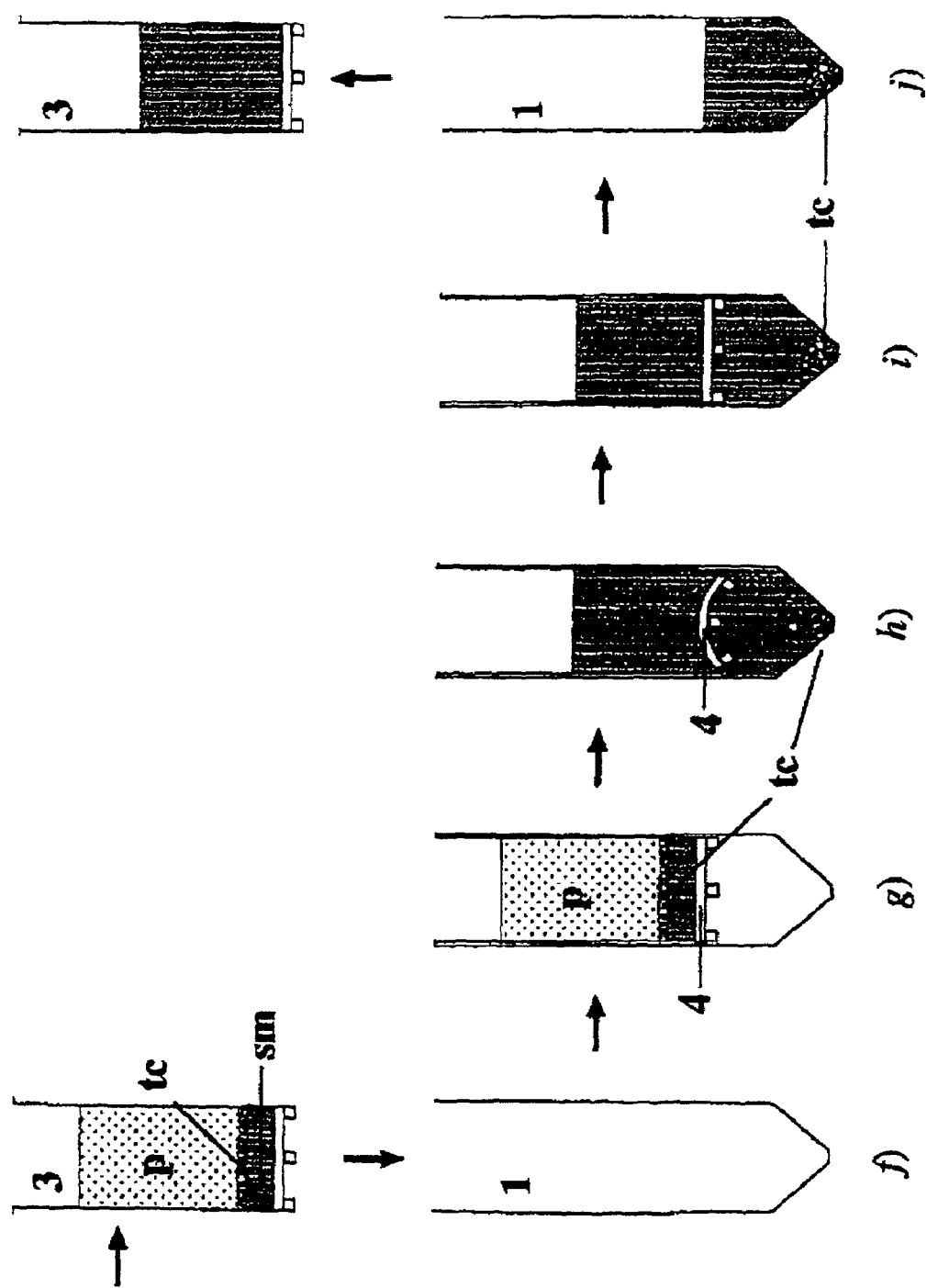
Figure 5:
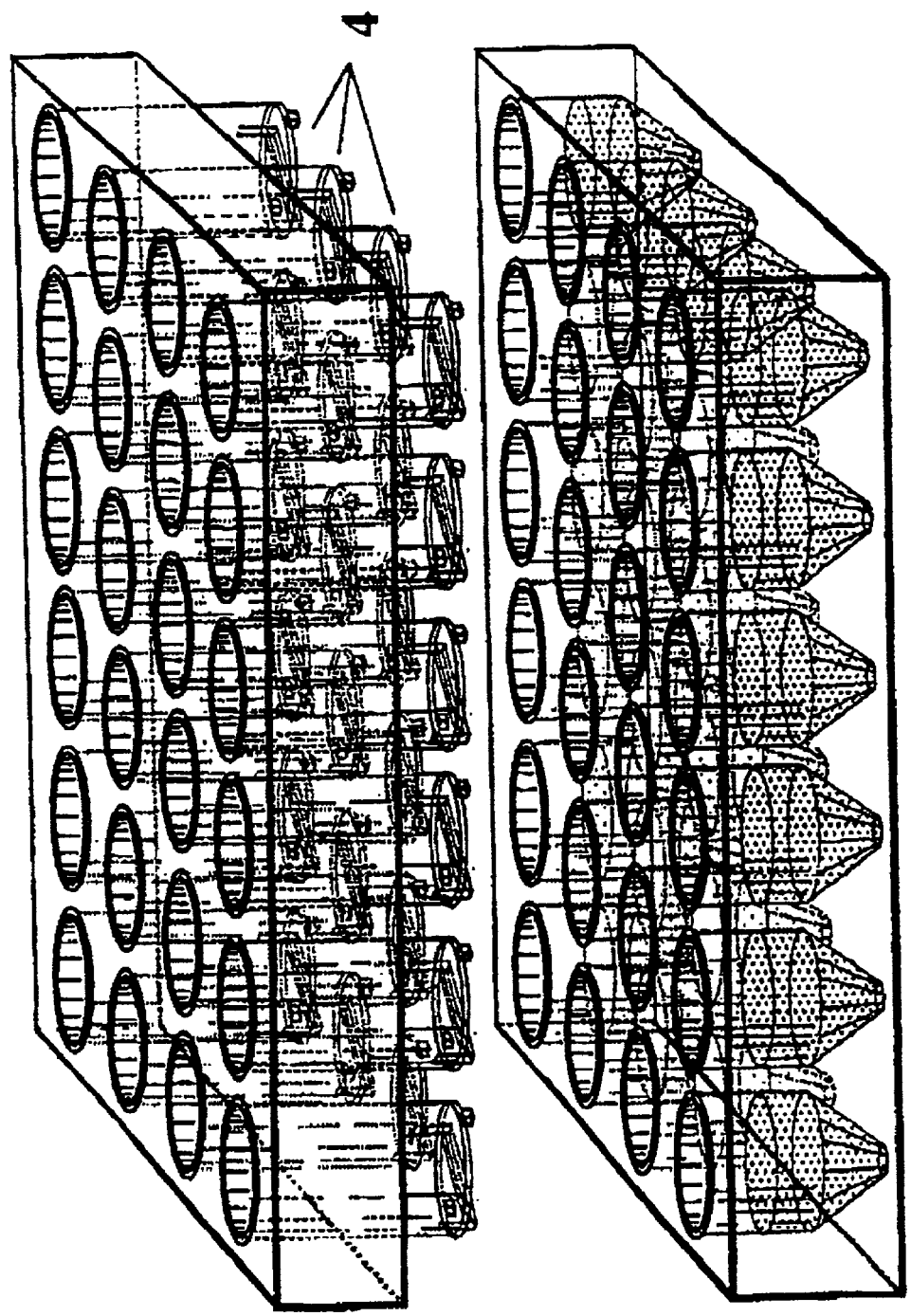
FIG. 5 shows an example of a flap insert for a microtiter plate with a plurality of flaps (4).

The RNA component of telomerase (hTR) is, differing from the use of Percoll with a density of 1.070 g/ml, undetectable in unspiked blood (compare FIG. 1). It is possible to detect hTR in the samples with 2 spiked prostate carcinoma cells (A) and with 4 spiked breast carcinoma cells (B) per ml of blood (black arrow). These tumor cells differ from the melanoma cell line T289 in that expression of the catalytic subunit (hTR) was not detectable (A) or was detectable only with $10^4$ tumor cells (B). Neither the prostate cell-specific marker PSA (prostate specific antigene) nor the epithelial cell-specific marker CK20 (cytokeratin 20) is detectable in the corresponding tumor cells. Actin serves as RT-PCR positive control.

Figure 8:
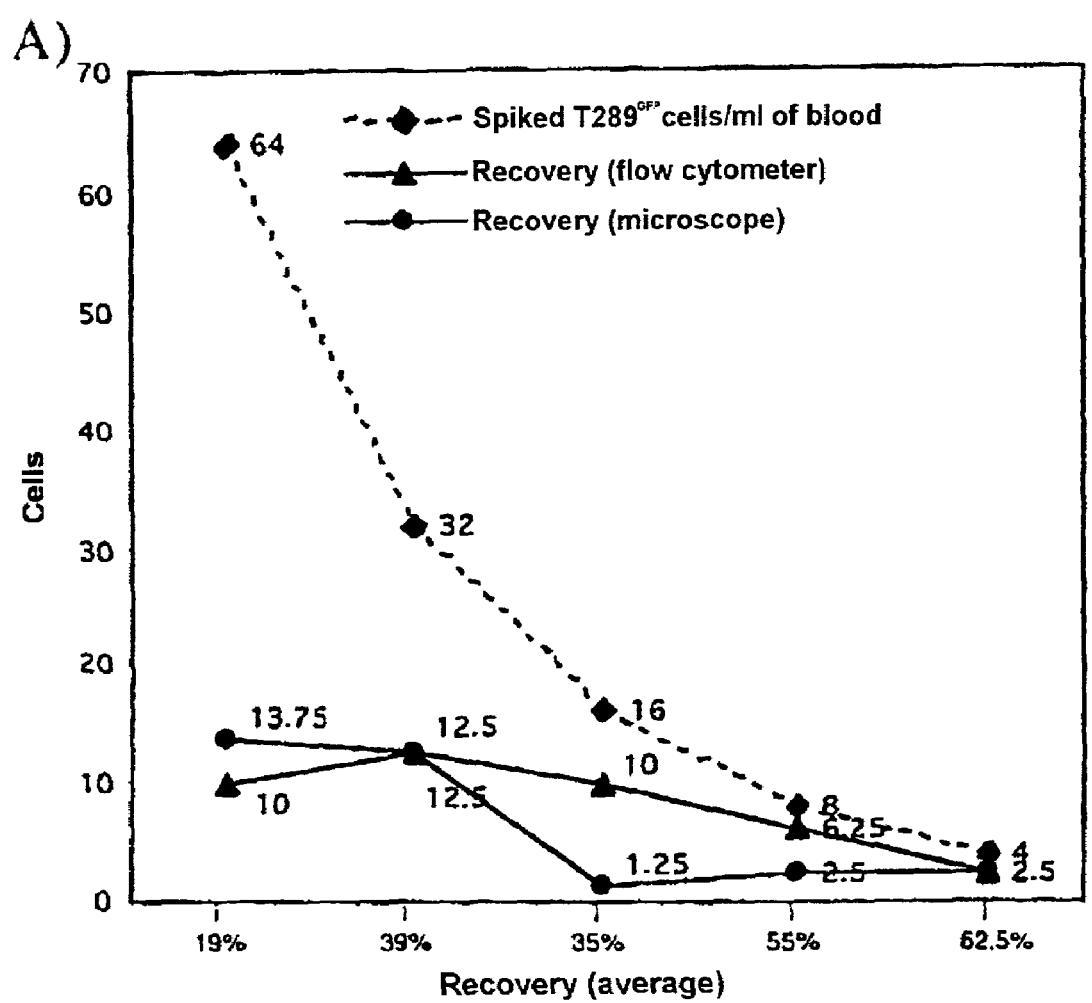
FIG. 8 shows the recovery rate for GFP-transfected melanoma cells admixed with blood from different (A, B) healthy donors, after enrichment with a cell separation medium having a density of 1.065 g/ml.

FIG. 8 shows the recovery rate for GFP-transfected melanoma cells (T289) with which blood samples from healthy donors were mixed (spiked). The spiked blood samples were then layered onto Percoll having a density of 1.065 g/ml and centrifuged, and the number of reisolated tumor cells (recovery) was determined by microscopy (-●-) and/or flow cytometry (-▲-). Since only about 75% for sample A and 50% for sample B of the GFP-transfected T289 cells were detectable in the flow cytometer, the recovery rates were corrected correspondingly. The recovery rate for spiked tumor cells depends on the particular blood donor (the blood samples of A) and B) are derived from different donors) and the cell line used, and is inversely proportional to the number of spiked tumor cells. It is possible that a repulsion reaction of the corresponding hematopoietic cells leads to lysis, aggregation and finally to loss of the spiked allogeneic tumor cells. B) additionally shows that the number of actually spiked tumor cells (-■-) is between [sic] 6%–37% less than the theoretically calculated number of spiked tumor cells (-◆-).

On inclusion of investigations, not shown here, with lung and breast carcinoma cells the average recovery rate with the enrichment method of the invention emerges as 46%±20% for 4–512 spiked cells (n=16) and 54%±20% (n=15) for ≦50 spiked cells.

This means that the recovery rate in the tumor cell enrichment method of the invention is approximately in the region of magnetic cell separators such as MACS, for which a recovery rate of about 30–58% is stated.

EXAMPLE 3

Initial clinical investigations on melanoma patients have shown that in 43% of patients with acute metastases and in 16% of patients without manifest acute oncosis (for example after resection of the tumors or after therapy) it was possible to detect telomerase in the disseminated circulating tumor cells in the blood which were enriched with the method of the invention. On the other hand, blood samples from 10 healthy donors which were investigated in parallel were negative.

This study on melanoma patients has therefore already shown an unambiguous correlation of the telomerase activity of disseminated circulating tumor cells in the blood and the metastasis status of the corresponding tumor patients.

EXAMPLE 4

4.1 Isolation of Cellular RNA

Figure 9:
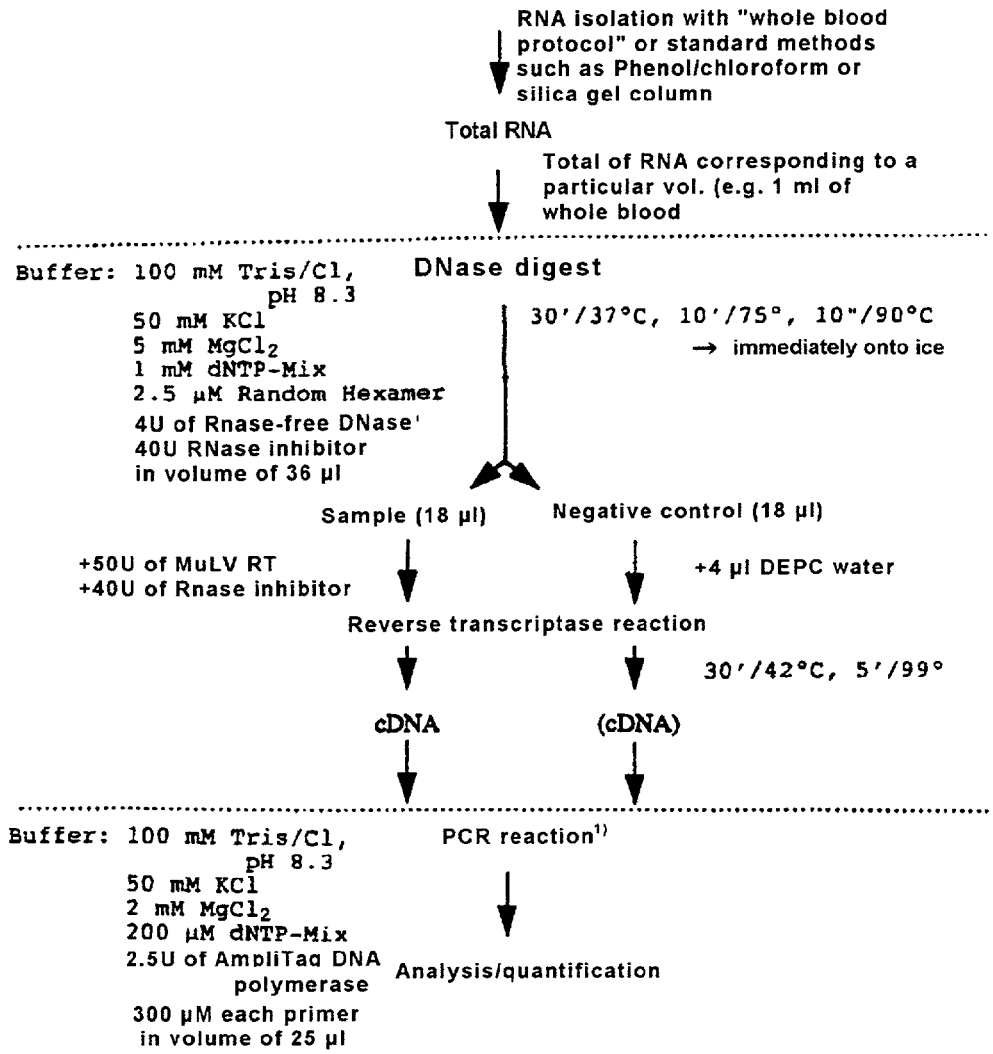
FIG. 9 shows a flow diagram for the RT-PCR.

The isolation of total cellular RNA took place by standard methods [Chomczynski et al. (1987) Anal Biochem 162, 156; Sambrook, J. et al. (1989). Cold Spring Harbor, N.Y., USA, Cold Spring Harbor Laboratory Press]. Peripheral blood was, as shown in FIG. 9, immediately after removal transferred into RNA lysis buffer (4M guanidinium isothiocyanate; 0.1M Tris-HCl, pH 7.5; 1% mercaptoethanol) and homogenized. The mixtures were either further processed immediately or stored at −70° C.

4.2 Reverse Transcription and Polymerase Chain Reaction (RT-PCR)

The RT-PCR was carried out with the GeneAmp® RNA-PCR kit (Perkin Elmer) in accordance with the manufacturer's instructions as shown in FIG. 9. Aliquots of the isolated total RNA from peripheral blood and cell lines were each previously hydrolyzed with 4 U of DNAse and 40 U of RNAse inhibitor (Boehringer, Mannheim) in 36 µl mixtures (in 100 mM Tris-HCl, pH 8.3; 50 mM KCl; 5 mM $MgCl_2$, 1 mM dNTP mix and 2.5 mM random hexamers) at 37° C. for 30 minutes and at 75° C. for 10 minutes, and subsequently the DNAse was inactivated at 90° C. for 10 minutes and then the reaction mixture was immediately put on ice.

The two oligonucleotide primers:

5' CTACCGGAAG AGTGTCTGGA GCAAGTTGCA AAGC 3' (hTRT1) and

5' GGCATACCGA CGCACGCAGT ACGTGTTCTG 3' (hTRT2)

were designed according to the sequence published by Nakamura et al. which codes for the catalytic subunit of human telomerase (Nakamura et al. (1997). Science 277: 955–9) and synthesized with an Applied Biosystem 380A synthesizer. The specificity of the hTRT1 and hTRT2 primers was checked by computer-assisted homology analysis on the nucleic acid sequences in the GenBank, EMBL, DDBJ and PDB databases by means of BLASTN 1.4.9 MP [Altschul, S. F. et al. (1990). J. Mol. Biol 215: 403–410].

Identical amounts of RNA were employed for the RT reaction for each experiment in order to match the amplification amounts. Contamination of the RNA preparations with genomic DNA was precluded by first subjecting each RNA-containing sample hydrolyzed with DNAse to the PCR described below, and checking for amplification. The RNA-containing sample with which no amplification product was detectable was employed for the following cDNA synthesis and PCR steps. Oligonucleotide primers for β-actin and TCR were employed as internal standard control. The reverse transcriptase reaction was carried out on 18 µl of the DNAse digest with addition of 50 U of MuLV reverse transcriptase and 40 U of RNase inhibitor at 42° C. for 30 minutes, and the reaction was stopped at 99° C. for 5 minutes. In the negative controls 4 µl of water were added in place of the enzymes.

The PCR was carried out as shown in FIG. 9 on 5 µl of the cDNA reaction using the following program: (97° C.: 15 seconds preheating); (97° C.: 15 seconds, 70° C.: 30 seconds [minus 0.5° C. per cycle], 72° C.: 30 seconds) 10 cycles; (94° C.: 15 seconds, 65° C.: 30 seconds [minus 0.5° C. per cycle], 72° C.: 30 seconds) 20 cycles; (94° C.: 15 seconds, 50° C.: 30 seconds 72° C.: 30 seconds [plus 15 seconds extension per cycle], 10 cycles; (72° C.: 7 minutes, final extension).

The amplification products were fractionated by gel electrophoresis on a 1.5% TAE agarose gel, stained with ethidium bromide and visualized under UV light and photodocumented.

EXAMPLE 5

Further spiking experiments as described in example 1 and 2 were carried out with the difference that normal non-siliconized polypropylene centrifugation vessels and Percoll with a density of 1.060 g/ml were used. The intention in these experiments was to determine firstly the degree of depletion of unwanted blood cells and secondly the degree of enrichment of tumor cells.

At about 80%–90% confluence, the tumor cell cultures of the breast cancer cell line MDMB 435s were trypsinized, and the cell suspension obtained was transferred into a ml centrifugation vessel and the latter was centrifuged at 500×g for 5 minutes. The cell pellet was resuspended in 0.5 ml.

For staining of the cell nucleus, 100 ml [sic] of the cell suspension (about $10^5$–$10^6$ cells) were mixed with ml [sic] of a DAPI solution (intercalating dye; 1 mg of 4',6'-diamidino-2-phenylindole dihydrochloride/ml of dimethyl sulfoxide [DMSO]) in a 1.5 ml centrifugation vessel and incubated at 37° C. and at 700 rpm in a Thermomixer (Eppendorf) for 10 minutes. The cells were then pelleted at 500×g for 5 minutes, resuspended in 1 ml of DPBE (1 ml of 0.1% BSA and 4 mM EDTA in Dulbecco PBS) and again centrifuged at 500×g for 5 minutes. The washing step was repeated twice. The cells were then adjusted to 2 000 cells/ml of DPBE with the aid of a particle counter (Z2, Beckman Coulter GmbH).

Triplicates of in each case 10, 20, 30, 40, 50, 60 and 70 ml [sic] of the DAPI-positive cell suspension were pipetted individually into the chambers of a 384 plate. The microtiter plate was then centrifuged at 700×g for 3 minutes, and the cells were counted with the aid of a fluorescence microscope (Axiovert 25, Zeiss, filter set 02, [extinction 358 nm, emission 460 nm]). A standard line was then formed (x=ml of DAPI-positive cell suspension; y=number of cells). The values of $r^2$ for the standard line were at least 0.95.

In the spiking experiments, an appropriate number of DAPI-positive cells was mixed in triplicates into 20 ml of full blood (Bayerisches Rotes Kreuz, BRK), and the whole blood was put in a 50 ml centrifugation vessel with a porous barrier (pore size 20–100 mm [sic]) into whose lower compartment 15 ml of Percoll with a density of 1.060 g/ml (at 4° C.) and an osmolarity of 280–300 mmol/kg had been introduced. The centrifugation vessel was then centrifuged at 4° C. and 1 000×g and 4° C. [sic] for 30 minutes.

After the centrifugation, the interphase cells were transferred with the aid of a 10 ml pipette into a fresh 50 ml centrifugation vessel. The upper compartment of the first centrifugation vessel was cautiously washed twice with 15 ml of DPBE, and the liquid was transferred into the second centrifugation vessel. The centrifugation vessel was then made up to 50 ml with DPBE and centrifuged at 200×g for 10 minutes. After the centrifugation, the supernatant was decanted off and the cell pellet was resuspended in 5 ml of erythrocyte lysis buffer (155 mM $NH_4Cl$, 10 mM $KHCO_3$ and 0.1 mM EDTA pH 7.3) and incubated at room temperature for 5 minutes. After completion of the erythrocyte lysis, the centrifugation vessel was made up to 50 ml of DPBE and again centrifuged at 200×g for 10 minutes, and the supernatant was decanted off. The cells were then taken up again in 50–200 ml of DPBE.

The cell suspension was then divided into two equal aliquots. One aliquot was put into the chamber of a 24 plate and the number of tumor cells in the microtiter plate were determined under the microscope. The total amount of cells in the second aliquot was determined using an automatic hematology analysis system (KX21, Sysmex).

Figure 10:
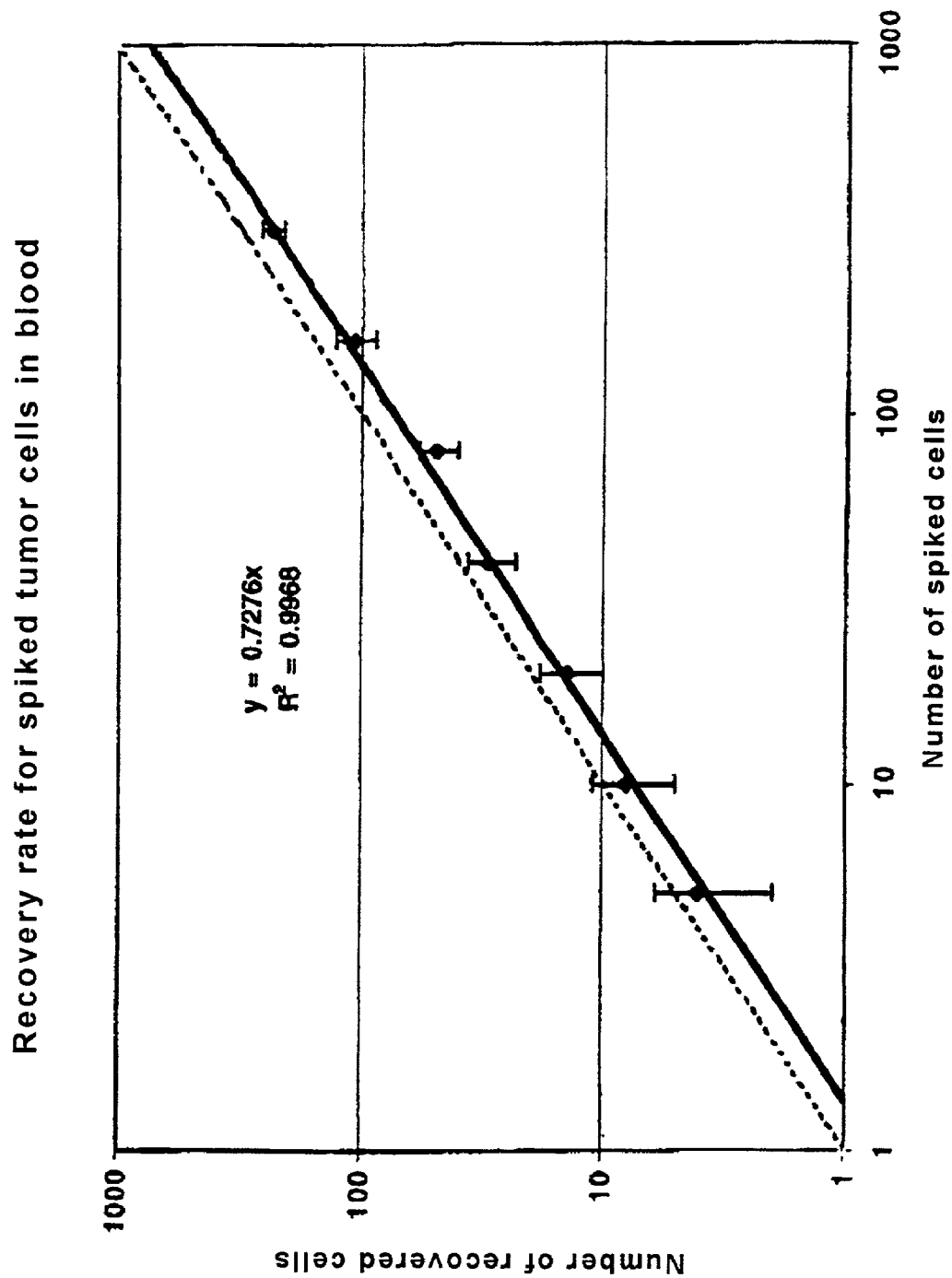
FIG. 10 shows the recovery rate for spiked tumor cells of the breast cancer cell line MDMB 435s in peripheral blood.

The experiments with a Percoll cell separation medium with a density of 1.060 g/ml show 1. a recovery rate of about 73% for the spiked tumor cells (5–320 spiked cells, FIG. 10) and 2. a depletion factor of about $10^3$ for leukocytes.

EXAMPLE 6

Figure 11:
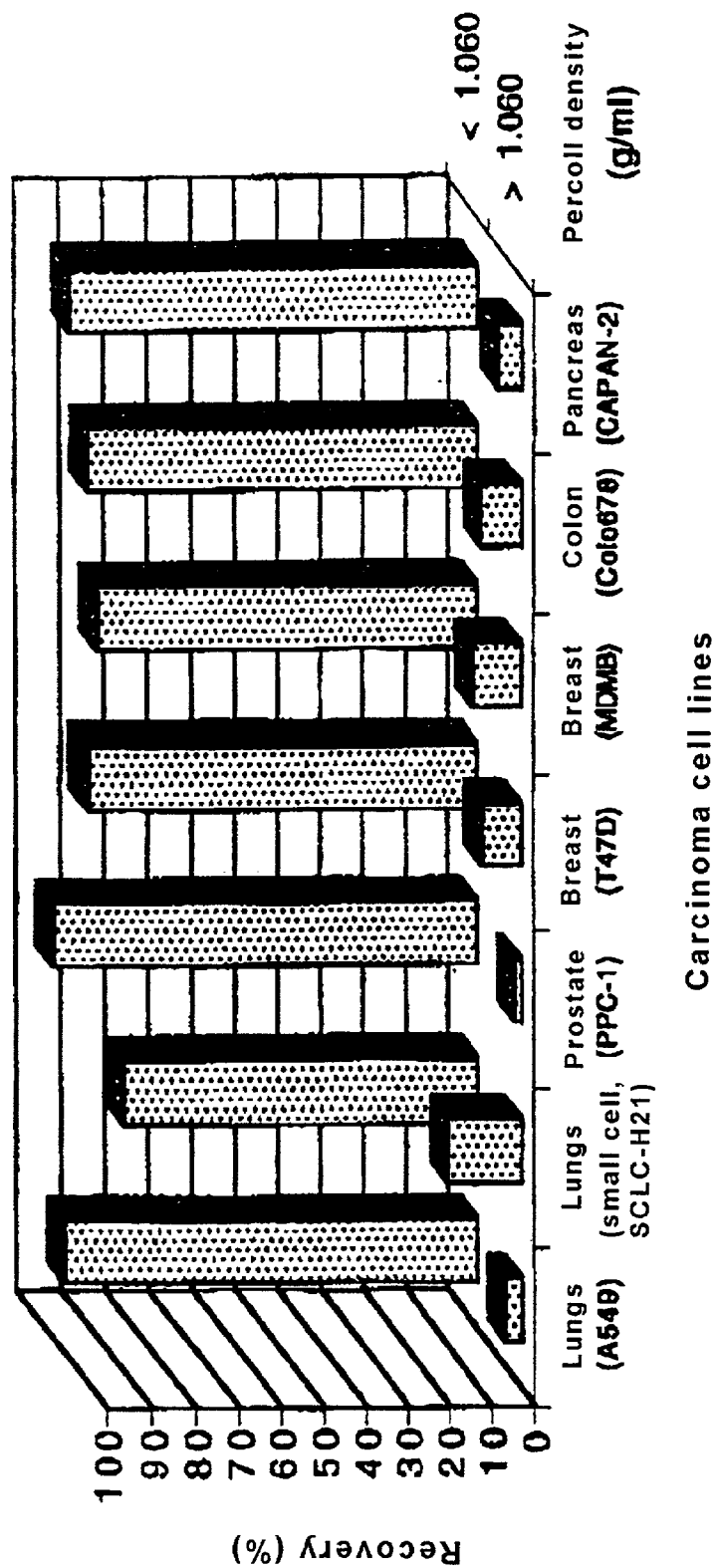
FIG. 11 shows the recovery rate for various carcinoma cell lines.

In order to establish whether further tumor cell lines can also be enriched with the method of the invention, the following investigations were carried out: tumor cell lines were cultivated in accordance with the ATCC instructions and harvested as described in example 2 and 5. A particle counter (Beckmann Coulter, Z2) was used to adjust the cell density of the suspension to $2×10^5$ cells/ml. 1 ml of this suspension was then cautiously put onto 5 ml of Percoll with a density of 1.060 g/ml in a 15 ml centrifugation vessel and a centrifugation was carried out at 1 000×g and 4° C. for 30 minutes. Then a 5 ml pipette was used to remove two 3 ml fractions and transfer each of them into two separate 15 ml centrifugation vessels. The first fraction contained the interphase cells, and the second fraction contained the remaining cells. The two fractions were centrifuged at 1 000×g for 10 minutes. The supernatant was then decanted off, the cell pellets were each resuspended in 1 ml of DPBE, and the number of cells in the two fractions was determined in a particle counter (Beckmann Coulter, Z2). FIG. 11 shows that the investigated cell lines from different organs such as lung (A549, SCLC-H21), prostate (PPC-1) breast (T47D, MDMB 435s) colon (colo678) and pancreas (CAPAN-2) have a density of <1.060 g/ml and are more than 90% found in the interphase. This experiment shows that at least all carcinoma cell lines have, irrespective of their origin, a density which allows the possibility of carrying out an enrichment of these cells with the method of the invention.

EXAMPLE 7

The method of the invention was used to carry out at the same time both immunocytological/immunocytochemical investigations and an RT-PCR for detecting telomerase in a number of patients with various manifest carcinomas. After informed consent had been obtained from the patients, up to 30 ml of whole blood were taken from the arm vein and between [sic] 10 to 20 ml were purified using the method of the invention, as described in example 5, and the cell pellet was washed twice in 10 ml of PBS and finally resuspended in 1 ml of PBS and 2 aliquots were formed. The first aliquot was transferred into RNA lysis buffer and stored at −70° C. until RNA was extracted and followed by RT-PCR, and the reactions were carried out as described in example 4. The second aliquot was subjected to immunocytological stainings. The number of cells applied to a slide corresponded to the equivalent of 10% of the originally purified amount of blood, i.e. with 20 ml of purified whole blood the equivalent of 2 ml of whole blood was concentrated and applied to the slide.

Three stainings were routinely carried out simultaneously:

1. a nuclear staining with an intercalating dye DAPI, 2. a staining of the epithelial cells with the anti-cytokeratin antibody cocktail (anti-cytokeratin Cam 5.2, B. D.) and 3. A staining of white blood cells with an anti-CD45 antibody in order to preclude nonspecific stainings.

The cell suspension was pipetted onto a slide treated with poly-L-lysine and dried at 4° C. overnight. To fix the cells, they were incubated with 100–200 µl of a 2% formaldehyde/DPBS solution at room temperature and then washed 3× with DPBS (with 0.01% NaAz, without EDTA). To permeabilize the cells, a 0.5% Triton X-100/DPBS (with 0.01% NaAz, without EDTA) solution was put on the slide at room temperature for 15 minutes, and then again washed 3× with DPBS (with 0.01% NaAz, without EDTA). To block nonspecific bindings and to stain the cell nuclei, the cells were incubated in 2% BSA/DPBS (with 0.01% NaAz, without EDTA)+1 µg/ml DAPI at room temperature for 30 minutes and washed 3× with DPBS (with 0.01% NaAz, without EDTA). 80 µl of the monoclonal mouse anti-cytokeratin antibody was put in a 1:500-fold dilution in DPBS (with 0.01% NaAz, without EDTA) on the cells at room temperature for 45 min. After washing three times with DPBS (with 0.01% NaAz, without EDTA), the slide was incubated with 50 µl of a phycoerythrin-conjugated anti-CD45 antibody (goat anti-mouse antibody) at room temperature for 45 min and then washed 3× with DPBS (with 0.01% NaAz, without EDTA). After staining with hematoxylin (50 µl, incubation for 1 min), the slides were washed 3× with $H_2O$ and covered. To check for nonspecific reactions, preparations from healthy blood donors were always included.

Evaluation of these investigations shows that in patients with advanced tumors of the gastrointestinal region, such as, for example, of the esophagus, stomach, colon, rectum and pancreas, and in patients with lung and breast tumors, in 11 of 14 cases cytokeratin-positive CD45-negative epithelial cells were found in the blood. These cells were arranged in the form of clusters and in some cases surrounded by CD45-positive cells, as is typical of cytospin preparations of circulating tumor cells. These cells are very probably tumor cells because epithelial cells are not to be expected in this frequency in the blood. The RT-PCR investigations were telomerase-positive in 93% (13/14) of these patients. In patients with locally restricted disease without signs of metastases, circulating epithelial cells were found in the blood in 50% of the cases (3/6). In 67% of these patients (4/6), telomerase was detectable. Investigations on healthy blood donors were epithelial- and telomerase-negative.

It was thus possible to show that it is possible to enrich efficiently from the blood not only spiked tumor cells of various cell lines but also circulating tumor cells from patients with various epithelial tumors (carcinomas).

The invention claimed is:

1. A method for simultaneously enriching tumor cells and depleting unwanted blood cells from a body fluid, comprising
    (a) centrifuging in a centrifugation vessel a cell separation medium overlaid with said body fluid, wherein said cell separation medium has a density in the range of from 1.055 to 1.065 g/ml, and wherein said centrifugation vessel is divided into an upper compartment and a lower compartment, and
    (b) introducing said cell separation medium into said lower compartment and said body fluid into said upper compartment, wherein said upper and lower compartments are divided by a porous barrier, filter, sieve, or flap, wherein said flap is a disk, wherein said disk is bent by centrifugation on two sides across a transverse strut.

2. The method of claim 1, wherein said cell separation medium has a density in the range of from 1.059 to 1.062 g/ml.

3. The method of claim 1, wherein said cell separation medium has a density of about 1.060 g/ml.

4. The method of claim 1, wherein said centrifuging is carried out at about 500 to 2000×g for about 10 to 30 minutes.

5. The method of claim 1, wherein said centrifuging is carried out at about 1000×g for about 20 to 30 minutes.

6. The method of claim 1, wherein said cell separation medium is selected from the group consisting of PERCOLL™ and FICOLL™.

7. The method of claim 1, wherein said body fluid comprises one or more substances which prevent aggregation of platelets onto tumor cells.

8. The method of claim 1, wherein said body fluid has been treated to remove substances which promote aggregation of platelets onto tumor cells.

9. The method of claim 1, wherein said body fluid is peripheral blood.

10. The method of claim 1, wherein said body fluid is peripheral blood mixed with an anticoagulant substance and diluted with a diluting medium.

11. The method of claim 9, wherein said peripheral blood is venous or arterial blood.

12. The method of claim 1, wherein said body fluid is selected from the group consisting of lymph, urine, exudates, transudates, spinal fluid, seminal fluid, saliva, fluids from natural or unnatural body cavities, bone marrow, and dispersed body tissue.

13. The method of claim 1, further comprising cooling a lower portion of said centrifugation vessel after said centrifuging and before removing an interphase enriched in tumor cells.

14. The method of claim 1, wherein said porous barrier, filter, sieve, or flap has a thickness of 0.5–10 mm.

15. The method of claim 1, wherein said porous barrier, filter, sieve, or flap has a thickness of 1–5 mm.

16. The method of claim 1, wherein said porous barrier, filter, or sieve has a pore size of 20–100 µm.

17. The method of claim 1, wherein said porous barrier, filter, or sieve has a pore size of 20–30 µm.

18. The method of claim 1, wherein said porous barrier, filter, sieve, or flap comprise a hydrophobic material or are coated with a hydrophobic material.

19. The method of claim 1, wherein said cell separation medium comprises a dye, wherein said dye allows said cell separation medium to distinguish from said overlying body fluid by color, and allows localization of an interphase enriched in tumor cells.

20. The method of claim 1, wherein said body fluid comprises non-tumor cells having telomerase activity and telomerase-positive tumor cells, and wherein said method further comprises forming an interphase enriched in said telomerase-positive tumor cells and depleted from said non-tumor cells having telomerase activity.

21. The method of claim 1, wherein said body fluid comprises tumor cells and blood stem cells, and wherein said method further comprises
    (a) forming an interphase enriched in said tumor cells and said blood stem cells, and
    (b) enriching or depleting said blood stem cells or said tumor cells.

22. The method of claim 21, wherein said cell separation medium has a density in the range of from 1.061 to 1.065 g/ml.

23. The method of claim 21, wherein said cell separation medium has a density of about 1.062 g/ml.

24. The method of claim 21, further comprising separating said tumor cells from said blood stem cells.

25. The method of claim 21, further comprising separating said tumor cells from said blood stem cells by immunoadsorption.

26. The method of claim 21, wherein said body fluid is selected from the group consisting of bone marrow and peripheral blood.

27. A kit for the separation of tumor cells from a body fluid, comprising a cell separation medium which has a density in the range of from 1.059 to 1.061 g/ml and a centrifugation vessel which is divided into an upper and a lower compartment and said compartments are divided by a porous barrier, a sieve or a flap, wherein said flap is a disk that bends by centrifugation on two sides across a transverse strut.

28. The kit of claim 27, wherein said cell separation medium has a density of about 1.060 g/ml.

29. The kit of claim 27, wherein said porous barrier, filter, sieve, or flap has a thickness of 0.5–10 mm.

30. The kit of claim 27, wherein said porous barrier, filter, sieve, or flap has a thickness of about 1–5 mm.

31. The kit of claim 27, wherein said porous barrier, filter, or sieve has a pore size of 20–100 µm.

32. The kit of claim 27, wherein said porous barrier, filter, or sieve has a pore size of 20–30 µm.

33. A centrifugation vessel comprising an upper and lower compartment, wherein the upper and lower compartments are divided by a flap and wherein said vessel contains a cell separation medium having a density in the range from 1.055 to 1.065 g/ml, and wherein said vessel flap is a disk that is bent by centrifugation on two sides across a transverse strut.

34. A centrifugation vessel as claimed in claim 33, wherein the flap is closed in the state when the centrifugation vessel is at rest and is opened during centrifugation.

35. A centrifugation vessel as claimed in claim 34, wherein the flap is open by centrifugal force during centrifugation.

36. The centrifugation vessel as claimed 33, wherein the flap has a higher density than a separation medium introduced into the lower compartment.

37. The centrifugation vessel as claimed 33, wherein the flap has a thickness of 0.5–10 mm.

38. The centrifugation vessel as claimed 33, wherein the flap has a thickness of 1–5 mm.

39. The centrifugation vessel as claimed in claim 33, wherein the flap is rigidly connected to the centrifugation vessel.

40. The centrifugation vessel as claimed in claim 33, wherein the flap forms a base of the upper compartment.

41. The centrifugation vessel as claimed in claim 33, wherein the vessel comprises an insert wherein the flap forms the base of the insert.

* * * * *